(12) United States Patent
Wu

(10) Patent No.: US 9,346,788 B2
(45) Date of Patent: May 24, 2016

(54) TRKA RECEPTOR TYROSINE KINASE ANTAGONISTS AND USES THEREOF

(71) Applicant: VM Oncology LLC, Fremont, CA (US)

(72) Inventor: Jay Jie-Qiang Wu, Fremont, CA (US)

(73) Assignee: VM Oncology, LLC, Fremont, CA (US)

( * ) Notice: Subject to any disclaimer, the term of this patent is extended or adjusted under 35 U.S.C. 154(b) by 0 days.

(21) Appl. No.: 14/614,917

(22) Filed: Feb. 5, 2015

(65) Prior Publication Data

US 2015/0218132 A1   Aug. 6, 2015

Related U.S. Application Data

(60) Provisional application No. 61/936,267, filed on Feb. 5, 2014.

(51) Int. Cl.
| | |
|---|---|
| C07D 257/04 | (2006.01) |
| C07D 401/04 | (2006.01) |
| C07D 295/116 | (2006.01) |
| A61K 31/495 | (2006.01) |
| A61K 31/496 | (2006.01) |
| A61K 31/4545 | (2006.01) |
| C07D 401/14 | (2006.01) |
| C07D 295/155 | (2006.01) |

(52) U.S. Cl.
CPC ............ *C07D 401/14* (2013.01); *C07D 257/04* (2013.01); *C07D 295/116* (2013.01); *C07D 295/155* (2013.01); *C07D 401/04* (2013.01)

(58) Field of Classification Search
None
See application file for complete search history.

(56) References Cited

U.S. PATENT DOCUMENTS

| | | |
|---|---|---|
| 3,845,770 A | 11/1974 | Theeuwes et al. |
| 3,916,899 A | 11/1975 | Theeuwes et al. |
| 4,765,539 A | 8/1988 | Noakes et al. |
| 5,112,598 A | 5/1992 | Biesalski |
| 5,556,611 A | 9/1996 | Biesalski |
| 5,698,155 A | 12/1997 | Grosswald et al. |

FOREIGN PATENT DOCUMENTS

| | | |
|---|---|---|
| WO | WO 00/73344 | 12/2000 |
| WO | WO 01/78698 | 10/2001 |
| WO | WO 2004/058184 | 7/2004 |
| WO | WO 2004/096122 | 11/2004 |
| WO | WO 2005/019266 | 3/2005 |
| WO | WO 2005 050203 | 6/2005 |
| WO | WO 2005/061540 | 7/2005 |
| WO | WO 2006/131952 | 12/2006 |

OTHER PUBLICATIONS

Burger's Medicinal Chemistry,edited by Manfred E. Wolff, 5th Ed. Part 1, pp. 975-977 (1995).*
Banker et al. "Modern Pharmaceutics", 3rd Ed. p. 596 (1996).*
Zhang et al.Nature Reviews, vol. 9, pp. 28-39 (2009).*
Stachel et al. J.Med.Chem.vol. 57,pp. 5800-5816 (2014).*
"A Study to Evaluate the Efficacy, Safety and Tolerability of CT327 in Atopic Dermatitis," retrieved online at https://clinicaltrials.gov/show/NCT01808157,%201%20, on Apr. 22, 2015, 4 pages.
Alberti L, et al., "RET and NTRK1 proto-oncogenes in human diseases," J Cell Physiol 195:168-186 (2003).
Alderman, "A Review of Cellulose Ethers in Hydrophilic Matrics for Oral Controlled-Release Dosage Forms," Int. J Pharm. Tech. & Prod. Mfr. 1984 5(3) 1-9.
Ardini, et al., "The TPM3-NTRK1 rearrangement is a recurring event in colorectal carcinoma and is associated with tumor sensitivity to TRKA kinase inhibition," Molecular Oncology 8:1495-1507 (2014).
Array Website, 2012.Available: http://www. arraybiopharrna. conm/ _documents/Publication/Pub ttachment5 8 7.pdf [Last accessed Jan. 22, 2014, 33 pages.
Bamba et al., "Release Mechanisms in Gelforming Sustained Release Preparations," Int. J Pharm., 2:307-315 (1979).
Beimfohr, C., et al., "NTRK1 re-arrangement in papillary thyroid carcinomas of children after the Chernobyl reactor accident," Int J Cancer Mar. 10,1999 15;80(6):842-7.
Bennett, et al., "A peripheral mononeuropathy in rat that produces disorders of pain sensation like those seen in man," Pain 1988;33(1):87-107.
Brown, M., et al., "Tanezumab reduces osteoarthritic hip pain: results of a randomized, double-blind, placebo-controlled phase III trial.," Arthritis Rheum 2013;65:1795-803.
Bundgaard, H. and Moss, J., "Prodrugs of Peptides IV: Bioreversible Derivatization of the Pyroglutamyl Group by N-Acylation and N-Aminomethylationto Effect Protection against Pyroglutamyl Aminopeptidase," J. Pharm. Sci. 78: 122-126 (1989).

(Continued)

*Primary Examiner* — Emily Bernhardt
(74) *Attorney, Agent, or Firm* — Cooley LLP

(57) ABSTRACT

The present disclosure relates to novel synthetic substituted heterocyclic compounds and pharmaceutical compositions containing the same, said compounds being capable of inhibiting or antagonizing TrkA receptor tyrosine kinases. In some aspects, the disclosure provides a compound having a structural formula (I):

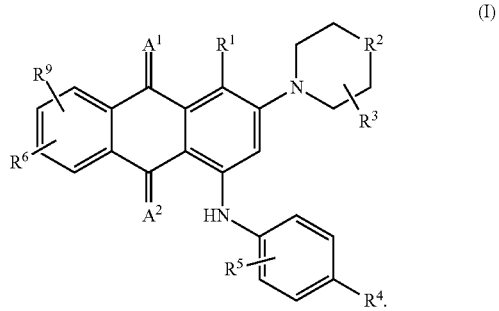

(I)

The disclosure further concerns the use of such compounds in the treatment and/or prevention of certain types of cancers, pain, inflammation, restenosis, atherosclerosis, psoriasis, thrombosis, Alzheimer's, a disease, disorder, injury, or malfunction relating to dysmyelination or demyelination.

20 Claims, No Drawings

(56) References Cited

OTHER PUBLICATIONS

Butti, et al., "A sequence analysis of the genomic regions involved in the rearrangements between TPM3 and NTRK1 genes producing TRK oncogenes in papillary thyroid carcinomas," Genomics. Jul. 1, 1995;28(1):15-24.
Calcutt NA, "Experimental models of painful diabetic neuropathy," J Neurol Sci. 2004;220(1-2):137-9.
Campos, X., "Nerve growth factor and its high-affinity receptor trkA participate in the control of vascular endothelial growth factor expression in epithelial ovarian cancer," Gynecol Oneal. Jan. 2007;104(1):168-75.
Chen-Tsai, C.P., "Correlations among neural cell adhesion molecule, nerve growth factor, and its receptors, TrkA, TrkB, TrkC, and p75, in perineural invasion by basal cell and cutaneous squamous cell carcinomas," Dermatol Surg 2004;30:1009-1016.
Cho, K., J., "Biomarkers for lower urinary tract dysfunction," International Journal of Urology (2013) 20, 13-20.
Cruz, C.D., "Neurotrophins in bladder function: what do we know and where do we go from here?," Neurourology and Urodynamics 33:39-45 (2014).
Dagnell et al., "Neurotrophins and neurotrophin receptors in pulmonary sarcoidosis—granulomas as a source of expression," Respiratory Research 2010, 11:156.
During et al., 1989, "Controlled release of dopamine from a polymeric brain implant: in vivo characterization," Ann. Neural. 25:351-356.
Euhus, et al., "ETV6-NTRK3—Trk-ing the primary event in human secretory breast cancer," Cancer Cell,2002; 347-8.
Fan, T.M., "Investigating TrkA expression in canine appendicular osteosarcoma," J Vet Intern Med May 2008;22:1181-1188.
Florenes, V.A., et al."Expression of activated TrkA protein in melanocytic tumors: relationship to cell proliferation and clinical outcome.," Am J Clin Pathol 2004;122:412-420.
Fornasari D., "Pain mechanisms inpatients with chronic pain.," Clin Drug Investig 2012; 32(suppl1):45-52.
Fragiadaki, M., et al., "Hyperglycemia causes renal cell damage via CCN2-induced activation of the TrkA receptor: implications for diabetic nephropathy," Diabetes. Sep. 2012, vol. 61 Issue 9, p. 2280-2288.
Frampton, "Crizotinib: a review of its use in the treatment of anaplastic lymphoma kinase-positive, advanced non-small cell lung cancer," Drugs 2013;73:2031-51.
Freund-Michel, V., et al., Immunology and Microbiology, "Inflammatory Diseases—A Modern Perspective", book edited by Amit Nagal, ISBN 978-953-307-444-3, Published: Dec. 16, 2011,"Chapter 5: Expression and Role of the TrkB Receptor in Pulmonary Inflammatory Diseases".
Ghilardi, J., et al., "Administration of a tropomyosin receptor kinase inhibitor attenuates sarcoma-induced nerve sprouting, neuroma formation and bone cancer pain," Mol Pain 2010;6:87-100.
Glaser, S., et al. "Cholangiocyte proliferation and liver fibrosis," Expert Rev Mol Med., 11:e7. doi:10.1017/S1462399409000994 [Expert Rev Mol Med. Author manuscript; available in PMC Apr. 30, 2009].
Greco, et al., "Rearrangements of NTRK1 gene in papillary thyroid carcinoma," Mol Cell Endocrinol 2010;321:44-9.
Gschwind, A., "The discovery of receptor tyrosine kinases: targets for cancer therapy," Nat Rev Cancer, 2004: 4:361-70.
H. Okada et al., "Synthesis and antitumor activities of prodrugs of benzoylphenylureas," Chem. Pharm. Bull. 1994, 42, 57-61.
Hondermarck, H., "Neurotrophins and their receptors in breast cancer," Cytokine Growth Factor Rev. 2012 3:357-65.
Howard et al., 1989, "Intracerebral drug delivery in rats with lesion-induced memory deficits." J Neurosurg. 71:105-112 (1989).
Hunt, J., "Origin of Gasoline Range Alkanes in the Deep Sea," Nature 254, 411-413 (Apr. 3, 1975) | doi:10.1038/254411a0; Received Jan. 10, 1975.
Iannone et al, "Increased expression of nerve growth factor (NGF) and high affinity NGF receptor (p140 TrkA) in human osteoarthritic chondrocytes," Rheumatology 41:1413-1418 (2002).
Ignyta, Inc. News Release. May 31, 2014. Website: http://finance.yahoo.com/news/ignyta-announces-interim-datarxdx-190000889.html, 4 pages.
Indo, et al., "Mutations in the TRKA/NGF receptor gene in patients with congenitalinsensitivity to pain with anhidrosis," Nat Genet 1996; 13:485.
Jarboe, J., et al., "Kinomic profiling approach identifies Trk as a novel radiation modulator.," Radiother Oneal. Jun. 2012; 103(3): 380-387.
Jin, et al., "DNA methylation-dependent regulation of TrkA, TrkB, and TrkC genes in human hepatocellular carcinoma," Biochem Biophys Res Commun. Mar. 4, 2011;406(1):89-95.
Kashyap, et al., "Down-regulation of nerve growth factor expression in the bladder by antisense oligonucleotides as new treatment for overactive bladder," J UrOl. Aug. 2013; 190(2):757-764.
Kim, J.S., et al., "Expression of nerve growth factor and matrix metallopeptidase-9/tissue inhibitor of metalloproteinase-1 in asthmatic patients," Journal of Asthma 2013 50(7):712-17.
Kim, S.H., and Chung, J.M., "An experimental model for peripheral neuropathy produced by segmental spinal nerve ligation in the rat," Pain. 1992;50(3):355-63).
Kishibe, K., "Production of nerve growth factor by mouse hepatocellular carcinoma cells and expression of TrkA in tumor-associated arteries in mice," Gastroenterology. Jun. 2002;122(7):1978-86.
Lane, "Tanezumab for the treatment of pain from osteoarthritis of the knee," N Eng! J Med 2010;363:1521-31.
Langer, 1990, "New methods of drug delivery," Science, 249:1527-1533.
Latremoliere, A. and Woolf, .J.C., "Central sensitization: a generator of pain hypersensitivity by central neural plasticiy," J Pain 2009; 10:895-926.
Lesage and Portenoy, "Trends in Cancer Pain Management," Journal of the Moffitt Cancer Center 1999;6(2):136-145.
Levy et al., "Inhibition of calcification of bioprosthetic heart valves by local controlled-release diphosphonate" 1985, Science 228: 190-192.
Li., et al., "SH2-B beta expression in alveolar macrophages in BAL fluid of asthmatic guinea pigs and its role in NGF-TrkA-mediated asthma.," Respirology (2009) 14, 60-68.
Lynch JJ, 3rd, et al., "An adenosine kinase inhibitor attenuates tactile allodynia in a rat model of diabetic neuropathic pain," Eur J Pharmacal. 1999;364(2-3): 141-6.
Malaguarnera, G., et al., "Serum markers of hepatocellular carcinoma," Digestive Diseases and Sciences, vol. 55, No. 10, (Oct. 2010), pp. 2744-2755, ISSN 0163-2116.
Martin-Zanca D et al., "A human oncogene formed by the fusion of truncated tropomyosin and protein tyrosine kinase sequences," Nature. Feb. 27-Mar. 5, 1987;319(6056):7438.
Matricon, "Peripheral contribution of NGF and ASIC1a to colonic hypersensitivity in a rat model of irritable bowel syndrome.," Neurogastroenterol Motif (2013) 25, e740-e754.
McCarthy, "Tropomyosin receptor kinase inhibitors: a patent update 2009-2013," Expert Opin Ther Pat. Jul. 2014;24(7):731-44.
Ochodnicky, P., "Nerve growth factor in bladder dysfunction: contributing factor, biomarker, and therapeutic target," Neurourology and Urodynamics 30:1227-1241 (2011).
Othumpangat, S., et al., "NGF is an Essential Survival Factor for Bronchial Epithelial Cells during Respiratory Syncytial Virus Infection," PLoS One 4(7): e6444 doi: 10.13 71 (journal.pone. 0006444) (2009), 13 pages.
Papatsoris, A., et al., "Manipulation of the nerve growth factor network in prostate cancer," Expert Opin 25 Investig Drugs, 2007;16:303-9.
Pathophysiology of cancer pain and opioid tolerance. In: The British Pain Society's Cancer Pain Management. The British Pain Society website. www.britishpainsociety.org. Published Jan. 2010. Accessed Jan. 29, 2013, 116 pages.
Pierotti, M.A., "Oncogenic rearrangements of the NTRK1/NGF receptor.," Cancer Lett 2006;232:90-8.
Portenoy RK and Dhingra LK, Assessment of Cancer Pain, In: Abrahm, J., ed. UpToDate. Waltham, MA: UpToDate; 2015, 7 pages.

(56) References Cited

OTHER PUBLICATIONS

Prakash, "Neurotrophins in lung health and disease," Expert 20 Rev Respir Med. Jun. 2010; 4(3): 395-411.

Qian, "Nerve growth factor, brain-derived neurotrophic factor and their highaffinity receptors are overexpressed in extramammary Paget's disease," J Cutan Pathol 2010: 37: 1150-1154.

Raile, K., et al.,"Glucose regulates expression of the nerve growth factor (NGF) receptors TrkA and p75NTR in rat islets and INS-1E beta-cells," Regulatory Peptides 135 (2006)30-38.

Rasi, et al., "Nerve growth factor involvement in liver cirrhosis and hepatocellular carcinoma," World J Gastroenterol Oct. 7, 2007; 13(37): 4986-4995, [retrieved online at http://www.wjgnet.com/1007-9327/full/v13/i37/4986.htm[Apr. 22, 2015 10:42:30 AM].

Ribatti, "Correlation between NGF/TrkA and microvascular density in human pterygium," Int. J Exp. Path. (2009), 90, 615-620.

Rubin, et al., "Congenital mesoblastic nephroma t(12;15) is associated with ETV6-NTRK3 gene fusion: cytogenetic and molecular relationship to congenital (infantile) fibrosarcoma," Am J Pathol, 1998;153:1451-8.

Santa Maria, P.L., "Tympanic membrane wound healing in rats assessed by transcriptome profiling.," Laryngoscope Oct. 2011; 121(10):2199-213.

Saudek et al., 1989, "A preliminary trial of the programmable implantable medication system for insulin delivery," N Engl. J Med. 321 :574-579 (1989).

Sciabas, G., M., "Overexpression of tropomysin-related kinase B in metastatic human pancreatic cancer cells," Clin Cancer Res., 2005;11:440-9.

Sefton, 1987, "Implantable pumps," CRC Crit Ref Biomed Eng. 14(3):201-240.

Seth, et al., "Nerve growth factor (NGF): a potential urinary biomarker for overactive bladder syndrome (OAB)?," BJU International,111:372-380, (2013).

Sevcik, MA, et al, "Anti-NGF therapy profoundly reduces bone cancer pain and the accompanying increase in markers of peripheral and central sensitization," Pain 115:128-141 (2005).

Shi, H., et al., "Effects of recombinant human nerve growth factor on cervical cancer," *African Journal of Biotechnology* vol. 10(38), pp. 7503-7509, Jul. 25, 2011.

Thiele, "On Trk—the TrkB signal transduction pathway is an increasingly important target in cancer biology," *Clin Cancer Res*, 2009; 15:5962-7.

Vaishnavi, A., et al., "Oncogenic and drug-sensitive NTRK1 rearrangements in lung cancer," Nat Med 2013;19:1469-72.

van Schijndel, J., "Three-cohort targeted gene screening reveals a non-synonymous TRKA polymorphism associated with schizophrenia.," J Psychiatr Res. Oct. 2009;43(15): 1195-9.

Verma et al., "Osmotically Controlled Oral Drug Delivery," Drug Dev. Ind. Pharm., 2000, 26:695-708.

Verschoyle et al., British J Cancer, 1999, 80, Suppl. 269, poster.

Viet, C.T., "Biologic mechanisms of oral cancer pain and implications for clinical therapy," *J Dent Res* 91(5):447-453, 2012.

Wang, X., et al., "Regulation of pro-inflammatory and pro-fibrotic factors by CCN2/CTGF in H9c2 cardiomyocytes," J Cell Commun Signal. Mar. 2010; 4(1): 15-23.

Weeraratna, A.T., Rational basis for Trk inhibition therapy for prostate cancer, *Prostate*, 2000:45:140-8.

Weinkauf, C., "Neurotrophin Receptor TrkC is an Entry Receptor for Trypanosoma cruzi in Neural, Glial, and Epithelial Cells," Infect Immun 2011;79:4081-7.

Weinkauf, C., and PereiraPerrin, M., "Trypanosoma cruzi Promotes Neuronal and Glial Cell Survival through the Neurotrophic Receptor TrkC," Infect Immun 2009; 77: 1368-75.

Wiesmann, C., "Crystal structure of nerve growth factor in complex with the ligand-binding domain of the TrkA receptor," Nature 401:184-188 (1999).

Wiesner T, et al., "Kinase fusions are frequent in Spitz tumors and spitzoid melanomas," Nat Commun. 2014; 5: 3116. doi:10.1038/ncomms4116, 20 pages.

Yang, X., Q., et al., "Clinical significance of nerve growth factor and tropomyosin-receptor-kinase signaling pathway in intrahepatic cholangiocarcinoma," *World J Gastroenterol* Apr. 14, 2014; 20(14): 4076-4084.

Yang, Y, , et al., "Nerve growth factor exacerbates allergic lung inflammation and airway remodeling in a rat model of chronic asthma," Exp Ther Med 6:1251-8 (2013).

Zhu, et al, "Nerve growth factor expression correlates with perineural invasion and pain in human pancreatic cancer," Journal of clinical oncology, 17:2419-2428 (1999).

\* cited by examiner

TRKA RECEPTOR TYROSINE KINASE ANTAGONISTS AND USES THEREOF

CROSS REFERENCE TO RELATED APPLICATIONS

The present Application claims the benefit of priority to U.S. Provisional Application No. 61/936,267, filed on Feb. 5, 2014, the entire contents of which are hereby incorporated by reference in their entirety for all purposes.

1. FIELD OF THE DISCLOSURE

The present disclosure relates to synthetic substituted heterocyclic compounds and pharmaceutical compositions containing the same that are capable of inhibiting or antagonizing protein kinase activities. The disclosure further concerns the use of such compounds in the treatment and/or prevention of certain types of cancers, itching, atopic dermatitis, scabies, pityriasis, inflammation, restenosis, atherosclerosis, psoriasis, thrombosis, Alzheimer's, pain, a disease, disorder, injury, or malfunction relating to dysmyelination or demyelination or the disease or disorder associated with abnormal activities of protein kinases.

2. BACKGROUND OF THE DISCLOSURE

Trk family proteins are receptor tyrosine kinases composed of three family members, TrkA, TrkB and TrkC. They bind with high affinity to, and mediate the signal transduction induced by the Neurotrophin family of ligands whose prototype members are Nerve Growth Factor (NGF), Brain-Derived Neurotrophic Factor (BDNF) and Neurotrophin 3-5 (NT 3-5). In addition, a co-receptor lacking enzymatic activity, p75, has been identified which binds all neurotrophines (NTs) with low affinity and regulates neurotrophin signaling. A critical role of the Trks and their ligands during the development of the central and peripheral nervous systems have been established through gene disruption studies in mice. In particular, TrkA-NGF interaction was shown as a requirement for the survival of certain peripheral neuron populations involved in mediating pain signaling. It has been shown that increased expression of TrkA also correlates with an increased level of pain in the case of pancreatic cancer (Zhu, et al, Journal of clinical oncology, 17:2419-2428 (1999)). Increased expression of NGF and TrkA was also observed in human osteoarthritis chondrocytes (Iannone et al, Rheumatology 41:1413-1418 (2002)).

TrkA (Troponyosin-receptor kinase A) is a cell surface receptor kinase containing an extracellular, a transmembrane, and a cytoplasmic kinase domain. The binding of a neurotrophin triggers oligomerization of the receptors, phosphorylation of tyrosine residues in the kinase domain, and activation of intercellular signaling pathways, including Ras/MAPK cascade, PI3K/AKT, and IP3-dependent Ca2+ release. Tyrosine kinase activity is an absolute requirement for signal transduction through this class of receptor. NGF receptors have been also found on a variety of cell types outside of the nervous system. For example, TrkA has been also found on human monocytes, T- and B-lymphocytes and mast cells.

There are several examples of either ant-TrkA antibodies or anti-NGF antibodies known in the art. For example, PCT Publication Nos. WO 2006/131952, WO 2005/061540 and EP 1181318 disclose use of anti-TrkA antibodies as effective analgesics in in-vivo animal models of inflammatory and neuropathic pain. PCT Application Nos. WO 01/78698, WO 2004/058184 and WO 2005/019266 disclose the use of an NGF antagonist for preventing or treating pain. PCT Application WO 2004/096122 describes a method for the treatment or the prevention of pain with co-administration of an anti-NGF antibody and an opioid analgesic. PCT Application WO 2006/137106 discloses a method for the treatment or the prevention of pain with co-administration of an anti-TrkA antibody and an opioid analgesic. In addition, profound or significantly attenuated reduction of bone pain caused by prostate cancer metastasis has been achieved by utilization of an anti-NGF antibody (Sevik, M A, et al, Pain 115:128-141 (2005)). Loss-of-function mutations in TrkA (NTRK1) lead to congenital insensitivity to pain with anhidrosis [*Nat Genet* 1996; 13:485-8] and the anti-NGF antibody tanezumab has demonstrated clinical efficacy in osteoarthritis pain and diabetic neuropathic pain [*N Engl J Med* 2010; 363:1521-31; *Arthritis Rheum* 2013; 65:1795-803]. Additionally, Trk inhibitors show excellent efficacy in preclinical models of pain [*Mol Pain* 2010; 6:87-100]. Array has recently demonstrated equivalent efficacy with allosteric TrkA-selective inhibitors in pain models, which have the potential to be safer than pan-Trk inhibitors as discussed later [Array Website, 2012. Available: http://www.arraybiopharrna.conm/_documents/Pubbcation/PubAttachment587.pdf [Last accessed 22 Jan. 2014].

There is some evidence that inhibition of Trks may be beneficial in the treatment of Alzheimer's disease. NGF and TrkA levels are elevated in airways of asthmatics (asthma) [*J Asthma* 2013; 50:712-17; *Respirology* (2009) 14, 60-68; and *PLoS ONE* 4(7): e6444. doi:10.1371/journal.pone.0006444] and may contribute to inflammation, hyperresponsiveness and remodeling. NGF and TrkA has also been shown to exacerbate ovalbumin-induced airway inflammation in rodents [*Exp Ther Med* 2013; 6:1251-8]. CT327 is a topical TrkA inhibitor that has been clinically evaluated by Creabilis for chronic pruritus in diseases such as atopic dermatitis, psoriasis and itch [http://clinicaltrials.gov/show/NCT01808157]. Inhibition of TrkA may have utility in the treatment of Chagas disease. *Trypanosoma cruzi*, the agent of Chagas' disease, utilizes Trk to invade various cell types in the human host [*Infect Immun* 2009; 77: 1368-75; *Infect Immun* 2011; 79:4081-7].

Selective inhibition of TrkA kinase activity may also have utility in the treatment of ear diseases [*Laryngoscope* 2011 October; 121(10):2199-213], liver cirrhosis and hepatocellular carcinoma [*World J Gastroenterol* 2007 Oct. 7; 13(37): 4986-4995], Pulmonary Inflammatory Diseases [*Immunology and Microbiology*>> "*Inflammatory Diseases—A Modern Perspective*", book edited by Amit Nagal, ISBN 978-953-307-444-3, Published: Dec. 16, 2011, Chapter 5: Expression and Role of the TrkA Receptor in Pulmonary Inflammatory Diseases], fibrosis [*J Cell Commun Signal. March* 2010; 4(1): 15-23. Patent Application: PCT/GB2004/004795], Pterygium [*Int. J. Exp. Path.* (2009), 90, 615-620], lung diseases [*Expert Rev Respir Med*. 2010 June; 4(3): 395-411.], pulmonary sarcoidosis [Dagnell et al. *Respiratory Research* 2010, 11:156], bladder dysfunction [*Neurourology and Urodynamics* 30:1227-1241 (2011); *BJU International* 111, 372-380; *J Urol.* 2013 August; 190(2): 757-764; *Neurourology and Urodynamics* 33:39-45 (2014)], lower urinary tract dysfunction [*International Journal of Urology* (2013) 20, 13-20], Paget's disease [*J Cutan Pathol* 2010: 37: 1150-1154], diabetic nephropathy [*Diabetes*. September 2012, Vol. 61 Issue 9, p 2280-2288; *Regulatory Peptides* 135 (2006) 30-38.], irritable bowel syndrome [*Neurogastroenterol Motil* (2013) 25, e740-e754], radiation protection [*Radiother Oncol.* 2012 June; 103 (3): 380-387].

Furthermore, pain, which can be caused by the disease itself or by treatments, is common in people with cancer, although not all people with cancer will experience pain. Approximately 30% to 50% of people with cancer experience pain while undergoing treatment, and 70% to 90% of people with advanced cancer experience pain [Lesage P. and Portenoy R K. *Cancer Control; Journal of the Moffitt Cancer Center* 1999; 6(2):136-145]. Cancer pain is a complex, temporally changing symptom which is the end result of mixed mechanism pain. It involves inflammatory, neuropathic, ischemic, and compression mechanisms at multiple sites [*Pathophysiology of cancer pain and opioid tolerance*. In: *The British Pain Society's Cancer Pain Management*. The British Pain Society website. www.britishpainsociety.org. Published January 2010. Accessed Jan. 29, 2013]. It is a subjective, heterogeneous experience that is modified by individual genetics, past history, mood, expectation, and culture. Cancer pain syndromes are categorized as acute and chronic based on onset and duration. Acute pain syndromes have a sudden, well-defined onset, an identifiable cause (e.g. surgery), subject to sympathetic output (fight or flight response), and are expected to improve with management. Chronic pain on the other hand, has a less distinct onset, has a prolonged and fluctuating course, and is largely driven by central sensitization and neuroplastic responses from acute injury [Fornasari D. *Pain mechanisms in patients with chronic pain. Clin Drug Investig* 2012; 32(suppl 1):45-52; Latremoliere A, Woolf C J. *Central sensitization: a generator of pain hypersensitivity by central neural plasticity. J Pain* 2009; 10:895-926]. It is often characterized by "pain flares" referred to as breakthrough pain [Portenoy R K, Dhingra L K. *Assessment of cancer pain*. In: Drews R E, ed. *UpToDate*. Waltham, Mass.: UpToDate; 2013].

The therapeutic implications of an effective Trk inhibitor may well go beyond pain therapy. A TrkA polymorphism has been identified to be associated with schizophrenia [*J Psychiatr Res.* 2009 October; 43(15):1195-9]. The subversion of this receptor and its signaling pathway in certain malignancies has also been documented. The potential utility of Trk inhibitors in oncology has been covered previously (for reviews, see, *Expert Opin Ther Pat.* 2014 July; 24(7):731-44; *Nat Rev Cancer,* 2004: 4:361-70; *Clin Cancer Res,* 2009; 15:5962-7). TrkA and/or Trk(B/C) have been implicated in the survival and metastasis of prostate [*Expert Opin Investig Drugs,* 2007; 16:303-9; *Prostate,* 2000:45:140-8], breast [*Cytokine Growth Factor Rev,* 2012; 23; 357-65], hepatocellular carcinoma (liver cancer) and liver cirrhosis [*World J Gastroenterol.* 2007 Oct. 7; 13(37):4986-95; *Gastroenterology.* 2002 June; 122(7):1978-86; *Biochem Biophys Res Commun.* 2011 Mar. 4; 406(1):89-95; *Digestive Diseases and Sciences, Vol.* 55, No. 10, (October 2010), pp. 2744-55, ISSN 0163-2116], intrahepatic cholangiocarcinoma [*World J Gastroenterol* 2014 Apr. 14; 20(14): 4076-4084], liver fibrosis [*Expert Rev Mol Med.;* 11: e7. doi:10.1017/S1462399409000994], ovarian cancer [*Gynecol Oncol.* 2007 January; 104(1):168-75], pancreatic cancers [*Clin Cancer Res.,* 2005; 11:440-9], oral cancer [*Dermatol Surg* 2004; 30:1009-1016] and oral cancer pain [*J Dent Res* 91(5):447-453, 2012], skin cancer [*Am J Clin Pathol* 2004; 122:412-420], cervical cancer [*African Journal of Biotechnology* Vol. 10(38), pp. 7503-7509, 25 Jul., 2011], bone cancer [*J Vet Intern Med* 2008; 22:1181-1188]. Other rare cancers such as congenital mesoblastic nephroma, infant fibrosarcoma [*Am J Pathol,* 1998; 153:1451-8] and secretory breast carcinoma [*Cancer Cell,* 2002; 347-8] carry Tel-TrkC gene rearrangements. Somatic rearrangements of TrkA have been detected in a small but consistent subset of papillary thyroid rumors [*Cancer Lett* 2006; 232:90-8; *Mol Cell Endocrinol* 2010; 321:44-9; *Genomics.* 1995 Jul. 1; 28(1):15-24; *Int J Cancer.* 1999 Mar. 15; 80(6):842-7].

An exciting new avenue in the field has recently opened with the discovery of oncogenic TrkA (NTRK1) rearrangements in a small subset of lung cancer patients [*Nat Med* 2013; 19:1469-72], and in colorectal cancer (as TPM3-TrkA fusion mutation) [*Mol Oncol.* 2014 Jun. 12. pii: S1574-7891 (14)00125-2]. Tumor samples from 3 out of 91 lung cancer patients without previously identified genetic alterations demonstrated evidence of TrkA gene (NTRK1) fusions. These gene fusion mutations are intracellular oncogenic proteins, and they have constitutive activated intracellular TrkA kinase activity and transformed fibroblast cells. TrkA (NTRK1), TrkB (NTRK2), or TrkC (NTRK3) fusions have also been identified in glioblastoma, spitz tumors, spitzoid melanomas, acute myelogenous leukemia and secretory breast cancer [Greco A, et al. *Mol Cell Endocrinol* 2009; Alberti L, et al. *J Cell Physiol* 2003; Martin-Zanca D et al. *Nature* 1986; Wiesner T, et al. *Nat Commun* 2013; Vaishnavi A, et al, *Nat Med* 2013]. The identification of this gene rearrangement or fusion mutations may enable a patient stratification approach, similar to that utilized effectively by Pfizer, enabling the rapid registration and approval of crizotinib [*Drugs* 2013; 73:2031-51].

In fact, a patient with TrkA-positive metastatic colorectal cancer was recently clinically treated with RXDX-101, a pan Trk inhibitor and achieved a partial response [Ignyta, Inc. News Release. May 31, 2014. Website: http://finance.yahoo-.com/news/ignyta-announces-interim-data-rxdx-190000889.html]. Our own search of public human cancer genomic databases uncovered that many types of human cancers have TrkA fusions or fusion mutations, for examples, breast cancer (e.g., CAL-51, CAMA-1 and other 3 human breast cancer cells from 5 patients), endometrial cancer (e.g., RK95-2 and other 7 human cancer cells from 8 patients), blood cancer (e.g., CML-T1 and other 3 cancer cells from 4 patients), liver cancer (SNU-878 and other 2 cancer cells from 3 patients), colorectal cancer (e.g., SNU-C4 and other 10 cancer cells from 11 patients), pancreatic cancer (e.g., panc 02.13 and panc 03.27 from 2 patients), and skin cancer (e.g., LOX IMVI and other 4 cancer cells from 5 patients), that a TrkA selective inhibitor like the ones disclosed in current disclosure or a compound of the present disclosure can be utilized to precisely inactive intracellular TrkA kinase activity in those constitutive activated intracellular oncogenic proteins, i.e., TrkA fusion mutations, and hence as an effective human cancer treatment therapy for the types of human cancers listed above.

The tyrosine kinase activity of Trk is believed to promote the unregulated activation of cell proliferation machinery. It is believed that inhibitors of TrkA, TrkB, or TrkC kinases, individually or in combination, have utility against some of the most common cancers such as brain, melanoma, multiple myeloma, squamous cell, bladder, gastric, pancreatic, breast, head, neck, esophageal, prostate, colorectal, lung, renal, ovarian, gynecological, thyroid cancer, and certain type of hematological malignancies. Lestaurtinib (CEP-701, Cephalon), an indolocarbazole inhibitor of several tyrosine kinases, including Flt-3 and TrkA, and CEP-751, a pan Trk inhibitor have been entered Phase II clinical trials for the treatment of acute myelogenous leukaemia (AML), pancreatic cancer and multiple myeloma (MM) and/or prostate cancer.

Of particular note are reports of aberrant expression of NGF and TrkA receptor kinase are implicated in the development and progression of human prostatic carcinoma and pancreatic ductal adenocarcinoma and activating chromosomal rearrangements of Trks in acute myelogenous leukemia (AML), thyroid and breast cancers and receptor point mutations predicted to be constitutively activating in colon tumors. In addition to these activation mechanisms, elevated Trk receptor and ligand have also been reported in a variety of tumor types including multiple myeloma, melanoma, neuroblastoma, ovarian and pancreatic carcinoma. The neurotrophins and their corresponding Trk receptor subtypes have been shown to exert a variety of pleiotropic responses on malignant cells, including enhanced tumor invasiveness and chemotaxis, activation of apoptosis, stimulation of clonal growth, and altered cell morphology. These effects have been observed in carcinomas of the prostate, breast, thyroid, colon, malignant melanomas, lung carcinomas, glioblastomas, pancreatic carcinoids and a wide variety of pediatric and neuro-ectodermal-derived tumors including Wilm's tumor, neuroblastomas and medulloblastomas. Neurotrophins and their receptor subtypes have been implicated in these cancers either through autocrine or paracrine mechanisms involving carcinoma cells and the surrounding parenchymal and stromal tissues. Overall, the oncogenic properties of Trk signaling in multiple tumor types makes the modulation of the Trk receptor signaling a potentially attractive therapeutic intervention point in different malignancies.

Besides antibodies, however, few TrkA inhibitors are known and very few (if any) show high TrkA kinase selectivity (including staurosporine derived TrkA inhibitors, CEP-751 and CEP-701). It has been rarely (if any) known in the art that a synthetic organic molecule or compound had been used as either direct TrkA or NGF inhibitor or antagonist for treatment or prevention of pain in particular. It may due mainly to the facts of difficulty in identifying potent and particularly selective anti-TrkA or anti-NGF small organic compounds, though the crystal structure of NGF in complex with the TrkA receptor has been determined (Nature 401:184-188 (1996) & 254:411 (1991)).

The therapeutic implications of an effective Trk inhibitor may well go beyond pain therapy. The subversion of this receptor and its signaling pathway in certain malignancies has also been documented. The tyrosine kinase activity of Trk is believed to promote the unregulated activation of cell proliferation machinery. It is believed that inhibitors of TrkA, TrkB, or TrkC kinases, individually or in combination, have utility against some of the most common cancers such as brain, melanoma, multiple myeloma, squamous cell, bladder, gastric, pancreatic, breast, head, neck, esophageal, prostate, colorectal, lung, renal, ovarian, gynecological, thyroid cancer, and certain type of hematological malignancies. Lestaurtinib (CEP-701, Cephalon), an indolocarbazole inhibitor of several tyrosine kinases, including Flt-3 and TrkA, and CEP-751, a pan Trk inhibitor have been entered Phase II clinical trials for the treatment of acute myelogenous leukemia (AML), pancreatic cancer and multiple myeloma (MM) and/or prostate cancer.

Due to the therapeutic promise associated with inhibiting TrkA, and the relative lack of potent and selective inhibitors, it is great need to discover the potent and particular isoform selective TrkA inhibitors, especially of orally active small synthetic molecules for possible treatment or prevention of the disease or disorders associated with TrkA activity.

3. SUMMARY OF THE DISCLOSURE

The object of the present disclosure is the use of a small synthetic molecule, and its salts or solvates or prodrug, as protein kinase inhibitor and/or antagonists, particular as NGF receptor TrkA inhibitor and/or antagonist for the preparation of a medicament for the treatment and/or prevention of diseases associated directly or indirectly with inhibiting TrkA, which including certain cancer (e.g., pancreatic cancer, gastric cancer, esophageal cancer, gastrointestinal cancer, colorectal cancer, lung (small cell and non-small cell) cancer, liver cancer, hepatocellular carcinoma, intrahepatic cholangiocarcinoma, brain cancer or human neuroblastoma, glioblastoma and medulloblastoma, retinoblastoma, leukemia, lymphoma, melanoma, malignant mesothelioma, breast cancer, bladder cancer, ovarian cancer, prostate cancer or metastasis, thyroid cancer, squamous cell carcinomas, spitz tumors, spitzoid melanomas, acute myelogenous leukemia, endometrial cancer, skin cancer, oral cancer, bone cancer, melanoma), itching, atopic dermatitis, scabies, pityriasis, inflammatory bowel disease, inflammatory arthritis, asthma, human airway diseases, respiratory disease, fibrotic disease, renal fibrosis, liver fibrosis, liver cirrhosis, restenosis, atherosclerosis, psoriasis, thrombosis, Chagas' disease, parasitic diseases, Alzheimer's, pain (i.e, reducing pain for a subject in need thereof, including acute pain, chronic pain, inflammatory pain, neuropathic pain, cancer pain, and generalized pain disorder), Pulmonary Inflammatory Diseases, pulmonary sarcoidosis, bladder dysfunction or lower urinary tract dysfunction, Paget's disease, diabetic nephropathy, irritable bowel syndrome, radiation, schizophrenia, a disease, disorder, injury, or malfunction relating to dysmyelination or demyelination or the disease or disorder associated with abnormal activities of protein kinases.

In one aspect, the present disclosure provides, among other things, small molecule compounds and their salts or solvates or prodrugs as NGF receptor TrkA inhibitor and/or antagonist for the preparation of a medicament for the treatment and/or prevention of diseases associated, directly or indirectly with modulation of activity or expression of TrkA protein kinase or activity in certain patient populations with following cancer types with TrkA-positive mutations, fusions or fusion mutations or genetically abnormal TrkA kinase activity, that can be clinically diagnosed by current or future diagnostic tools, for examples, pancreatic cancer, prostate cancer or metastasis, breast cancer, hepatocellular carcinoma, intrahepatic cholangiocarcinoma, liver cancer, ovarian cancer, thyroid cancer, lung (small cell and non-small cell) cancer, colorectal cancer, glioblastoma, spitz tumors, spitzoid melanomas, acute myelogenous leukemia, endometrial cancer, skin cancer, oral cancer, bone cancer, melanoma, gastric cancer, esophageal cancer, gastrointestinal cancer, brain cancer or human neuroblastoma, medulloblastoma, retinoblastoma, leukemia, lymphoma, malignant mesothelioma, bladder cancer, squamous cell carcinomas.

In one aspect, the present disclosure provides compounds having structural Formula (I):

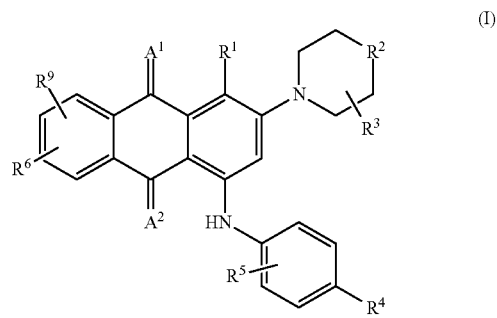

or a salt, solvate, ester, or prodrug thereof;
wherein:
  $A^1$ and $A^2$ are independently oxygen or sulfur;
  $R^1$ represents $NH_2$ or $R^7$;
  $R^2$ represents $NR^7$ or $CR^7R^{10}$;
  $R^3$, $R^5$, $R^6$, and $R^9$ are independently $R^7$;
  or alternatively, $R^6$ and $R^9$, taken together with the atom(s) to which they are attached, form a 3 to 6 membered optionally substituted heteroclcylic group containing one or more heteroatoms selected from the group consisting of nitrogen, oxygen, and sulfur;
  $R^4$ represents halogen, CN, $NO_2$, $CF_3$, —$(CHR)_nCOOR^{11}$, —$(CHR)_nSO_2R^{11}$, $C_{1-4}$ haloalkyl, —$OC_{1-4}$-haloalkyl, $C_{2-6}$ alkyl, $C_{2-6}$ alkenyl, $C_{2-6}$ alkynyl, —$(CHR)_nC_{6-10}$ aryl, —$(CHR)_nC_{5-8}$ heterocycle, —$(CHR)_nC_{3-8}$ cycloalkyl, —O—$C_{6-10}$ aryl, —O—$C_{5-10}$ heterocycle, —$(CHR)_nC(O)CF_3$, —$(CHR)_nC(OH)(CF_3)_2$, —$(CH_2)_n$halogen, —$OR_{10}$, —$NR^{11}R^{12}$, —$NR^aCOR^{11}$, —$NR^aCOOR^{11}$, —$NR^aSO_2R^{11}$, —$NR^aCONR^{11}R^{12}$, —$COR^{11}$, tetrazole, —$(CHR)_n$tetrazole, —S—$C_{1-6}$ alkyl, or —$CONR^{11}R^{12}$, wherein each said alkyl, alkenyl, alkynyl, aryl, cycloalkyl and heterocycle is independently optionally substituted with 1 to 2 groups of $R^8$;
  or alternatively, $R^4$ and $R^5$, taken together with the atom(s) to which they are attached, form a 3 to 6 membered optionally substituted heteroclcylic group containing one or more heteroatoms selected from the group consisting of nitrogen, oxygen, and sulfur;
  $R^7$ and $R^{10}$ are independently selected from the group consisting of hydrogen, halogen, CN, $NH_2$, $NO_2$, $C_{1-4}$ haloalkyl, —$OC_{1-4}$ haloalkyl, $C_{1-6}$ alkyl, $C_{2-6}$ alkenyl, $C_{2-6}$ alkynyl, —$(CHR)_nC_{6-10}$ aryl, —$(CHR)_nC_{5-8}$ heterocycle, —$(CHR)_nC_{3-8}$ cycloalkyl, —O—$C_{6-10}$ aryl, —O—$C_{5-10}$ heterocycle, —$C(O)CF_3$, —$(CH_2)_n$halogen, —$(CHR)_n$—$(O)_n$—$C(=O)R^8$, —$(CHR)_n$—$(S)_n$—$C(=O)R^8$, —$OR^a$, —$NR^{11}R^{12}$, —$NR^aCOR^{11}$, —$NR^aCOOR^a$, —$NR^aSO_2R$, —$NR^aCONR^{11}R^{12}$, —$COR^a$, —$(CHR)_nCOOR^a$, —S—$C_{1-6}$ alkyl, and —$CONR^{11}R^{12}$, wherein each said alkyl, alkenyl, alkynyl, aryl, cycloalkyl and heterocycle is independently optionally substituted with 1 to 2 groups of $R^8$;
  $R^{11}$ and $R^{12}$ are independently selected from the group consisting of hydrogen, $N(R^a)C(=O)R$, halogen, CN, $NH_2$, $NHR^a$, $NO_2$, $C_{1-4}$ haloalkyl, —$OC_{1-4}$ haloalkyl, $C_{1-6}$ alkyl, $C_{2-8}$ alkenyl, —S—$C_{1-6}$ alkyl, —$C(=O)$—$(O)_n$—$R^a$, —$(CHR)_n$—$(O)_n$—$C(=O)R^8$, —$(CHR)_n$—$(S)_n$—$C(=O)R^8$, —$OR^a$, —$(CHR)_nC_{3-10}$ cycloalkyl, —$(CHR)_nC_{6-10}$ aryl, —$(CHR)_nC_{5-10}$ heteroaryl, and —$(CHR)_nC_{5-10}$ heterocycle, wherein each said alkyl, alkenyl, cycloalkyl, aryl, heteroaryl and heterocycle is independently optionally substituted with 1 to 2 groups of $R^8$, and wherein one or more carbon atoms of said alkyl may be replaced with one or more heteroatoms selected from the group consisting of nitrogen, oxygen, and sulfur;
  or alternatively, $R^{11}$ and $R^{12}$, taken together with the atom(s) to which they are attached, form a 3 to 6 membered optionally substituted heteroclcylic group containing one or more heteroatoms selected from the group consisting of nitrogen, oxygen, and sulfur; wherein the optional substituent is $R^8$; and
  R each independently represents hydrogen, halogen, CN, $NO_2$, $NH_2$, or $C_{1-6}$ alkyl;
  $R^a$ each independently represents hydrogen or $C_{1-6}$ alkyl;
  $R^8$ each independently represents $C_{1-6}$ alkyl, halogen, CN, $NO_2$, $NH_2$, $NHR^a$, $SO_2R^{11}$, or $NR^aSO_2R^{11}$; and
  n represents an integer from 0 to 3;

with the following provisos:
  when $R^2$ is $CH_2$, $R^4$ is not H or $CH_3$;
  when $R^2$ is $NCH_2CH_2OH$, (a) $R^4$ is not H or $OCH_3$, or (b) $R^5$ is not $OCH_3$; and
  when $R^2$ is $N(CH_3)$, $R^4$ is not H, $CH_3$, $OCH_3$, or F.

In one embodiment of formula (I), $R^1$ is selected from the group consisting of hydrogen, —$(CH_2)_n$halogen, —CN, —$CH_3$, $NH_2$, $NHR^a$, and —$C_{1-3}$ alkyl.

In one embodiment of formula (I), $R^4$ is selected from the group consisting of —$C(O)OR^{11}$, —$SO_2NHC(=O)CH_3$, —$C(CF_3)(CF_3)OH$, —$SO_2NH_2$, —$C(O)NR^{11}R^{12}$, —CN, —$CF_3$, —$NO_2$, —$C(O)CF_3$, $(CH_2)_n$halogen,

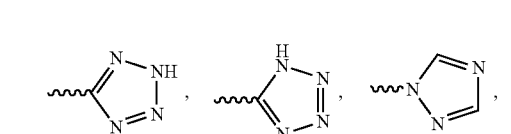

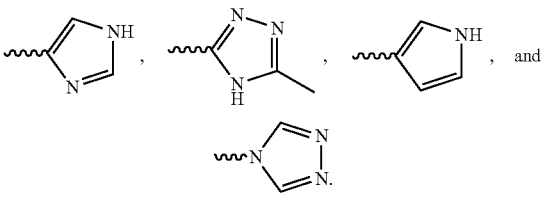

In one embodiment of formula (I), $R^3$, $R^5$, $R^6$, and $R^9$ are hydrogen.

In one embodiment of formula (I), $R^2$ is selected from

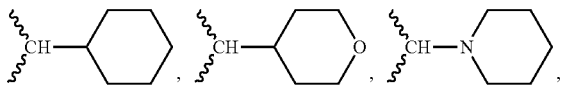

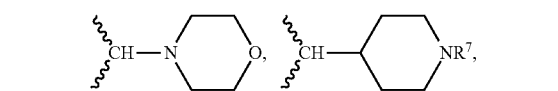

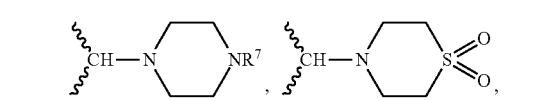

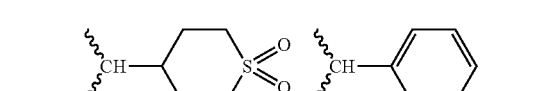

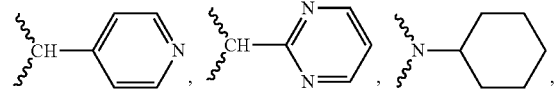

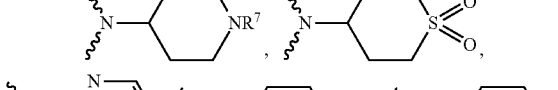

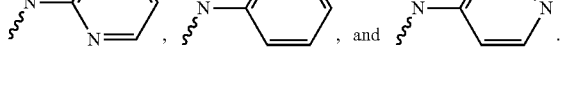

In another aspect, the present disclosure provides compounds having structural Formula (II):

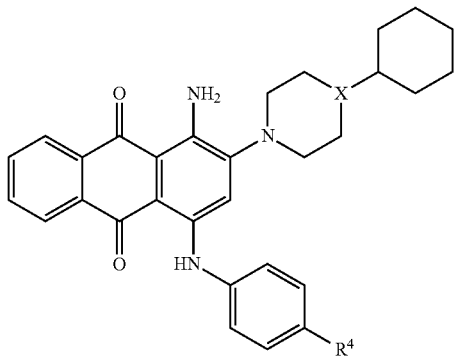

(II)

or a salt, solvate, ester, or prodrug thereof;
wherein:

X represents N or CH;

$R^4$ represents carboxy bioisostere selected from —$(CHR)_nCOOR^{11}$, —$(CHR)_nSO_2R^{11}$, —$(CHR)_nC_{5-8}$ heterocycle, or —$(CHR)_nC(OH)(CF_3)_2$, wherein each said heterocycle is independently optionally substituted with 1 to 2 groups of $R^8$;

$R^{11}$ is independently selected from the group consisting of hydrogen, $C_{1-6}$ alkyl, $NH_2$, $NHR^a$, and $NR^aC(=O)R$ wherein each said alkyl is independently optionally substituted with 1 to 2 groups of $R^8$, and wherein one carbon atom of said alkyl may be replaced with one heteroatom selected from the group consisting of nitrogen, oxygen, and sulfur;

$R^8$ each independently represents $C_{1-6}$ alkyl, halogen, CN, $NO_2$, $NH_2$, $NHR^a$, $SO_2R^{11}$, or $NR^aSO_2R^{11}$;

R each independently represents hydrogen, halogen, CN, $NO_2$, $NH_2$, or $C_{1-6}$ alkyl;

$R^a$ each independently represents hydrogen or $C_{1-6}$ alkyl; and n represents 0.

In one embodiment of formula (II), X represents N.

In one embodiment of formula (II), $R^4$ represents —$COOR^{11}$, wherein $R^{11}$ is hydrogen. In one embodiment of formula (II), $R^4$ represents —$COOR^{11}$, wherein $R^{11}$ is $C_{1-6}$ alkyl. In some embodiments of formula (II), $R^4$ represents —$COOR^{11}$, wherein $R^{11}$ is $C_{1-6}$ alkyl where one carbon atom of said $C_{1-6}$ alkyl is replaced with one nitrogen atom.

In one embodiment of formula (II), X represents N and $R^4$ represents —$COOR^{11}$, wherein $R^{11}$ is hydrogen.

In another embodiment of formula (II), $R^4$ represents —$SO_2R^{11}$, wherein $R^{11}$ is $NH_2$ or $NR^aC(=O)R$. In some embodiments of formula (II), $R^4$ represents —$SO_2R^{11}$, wherein $R^{11}$ is $NHC(=O)R$ and wherein R is $C_{1-6}$ alkyl.

In one embodiment of formula (II), $R^4$ represents $C_5$ heterocycle, wherein the heterocycle is a tetrazole.

In another aspect, the present disclosure provides pharmaceutical compositions comprising one or more compounds as described above or a salt, solvate, ester, prodrug, or physiologically functional derivative thereof; and a pharmaceutically acceptable vehicle.

In still another aspect, the present disclosure provides methods for selectively inhibiting or antagonizing NGF receptor TrkA for treatment and/or prevention of certain disease, disorder, symptom or condition including cancer (e.g., pancreatic cancer, gastric cancer, esophageal cancer, gastrointestinal cancer, colorectal cancer, lung cancer, liver cancer, brain cancer or human neuroblastoma, glioblastoma and medulloblastoma, retinoblastoma, leukemia, lymphoma, melanoma, malignant mesothelioma, breast cancer, bladder cancer, ovarian cancer, prostate cancer, thyroid cancer, squamous cell carcinomas, itching, atopic dermatitis, scabies, pityriasis, inflammatory bowel disease, inflammatory arthritis, asthma, human airway diseases, restenosis, atherosclerosis, psoriasis, thrombosis, Chagas' disease, parasitic diseases, Alzheimer's, pain, a disease, disorder, injury, or malfunction relating to dysmyelination or demyelination or the disease or disorder associated with abnormal activities of protein kinases, with therapeutic effective amount of the compound as described above, or a salt, solvate, or physiologically functional derivative thereof.

In still another aspect, the present disclosure provides methods for treatment and/or prevention of certain cancer (e.g., pancreatic cancer, gastric cancer, esophageal cancer, gastrointestinal cancer, colorectal cancer, lung cancer, liver cancer, brain cancer or human neuroblastoma, glioblastoma and medulloblastoma, retinoblastoma, leukemia, lymphoma, melanoma, malignant mesothelioma, breast cancer, bladder cancer, ovarian cancer, prostate cancer, thyroid cancer, squamous cell carcinomas, itching, atopic dermatitis, scabies, pityriasis, inflammatory bowel disease, inflammatory arthritis, asthma, human airway diseases, restenosis, atherosclerosis, psoriasis, thrombosis, Chagas' disease, parasitic diseases, Alzheimer's, pain, a disease, disorder, injury, or malfunction relating to dysmyelination or demyelination or the disease or disorder associated with abnormal activities of protein kinases, with combination of (a) therapeutic effective amount of the compound as described above, or a salt, solvate, or ester, prodrug, or physiologically functional derivative thereof, and either (b1) an opioid analgesic or at least one analgesic agent that acts by a mechanism different from a TrkA antagonist or (b2) an existing or proved anti-cancer agent or at least one existing or proved anti-cancer agent.

Additional embodiments include a combination of any of the foregoing embodiments and one or more pharmaceutically acceptable excipients. Other embodiments include a dosage form, such as a solid or semi-solid dosage form, comprising any of the foregoing crystal forms, amorphous forms, or combinations. In yet other embodiments, a dosage form comprising any of the foregoing crystal forms, amorphous forms, or combinations comprises one or more of a tablet, hard capsule, soft capsule, powder, suppository, and gel, or one or more of an injectable form, a transdermal patch, a sprayable form, and an implantable depot.

Other embodiments are a use of any of the foregoing embodiments in making a dosage form for inhibiting, or for inhibiting, a NGF receptor, TrkA. Still other embodiments are a use of any of the foregoing embodiments in making a dosage form for treating a disorder, disease or condition selected from the group consisting of pain (i.e, reducing pain for a subject in need thereof, including acute pain, chronic pain, inflammatory pain, neuropathic pain, cancer pain, and generalized pain disorder), cancer (e.g., pancreatic cancer, prostate cancer or metastasis, breast cancer, hepatocellular carcinoma, intrahepatic cholangiocarcinoma, liver cancer, ovarian cancer, thyroid cancer, lung (small cell and non-small cell) cancer, colorectal cancer, glioblastoma, spitz tumors, spitzoid melanomas, acute myelogenous leukemia, endometrial cancer, skin cancer, oral cancer, bone cancer, melanoma, gastric cancer, esophageal cancer, gastrointestinal cancer, brain cancer or human neuroblastoma, medulloblastoma, retinoblastoma, leukemia, lymphoma, malignant mesothelioma, bladder cancer, squamous cell carcinomas), atopic dermatitis, psoriasis, skin diseases, itch, liver fibrosis, liver cirrhosis, scabies, pityriasis, inflammatory bowel disease, inflammatory arthritis, asthma, human airway diseases, Chagas' disease, parasitic diseases, Alzheimer's, restenosis, atherosclerosis, thrombosis, liver cirrhosis, liver fibrosis, Pulmonary Inflammatory Diseases, pulmonary sarcoidosis, bladder dysfunction or lower urinary tract dysfunction, Paget's disease, diabetic nephropathy, irritable bowel syndrome, radiation, schizophrenia, or a disease, disorder or injury relating to dysmyelination or demyelination or the disease or disorder associated with abnormal activities of TrkA protein kinases or fusions or mutations of TrkA (NTRK1) protein, with therapeutic effective amount of the compound as described above, or a salt, solvate, or physiologically functional derivative thereof.

In another aspect, the disclosure provides pharmaceutical compositions comprising the compound described above, and a pharmaceutically acceptable vehicle.

In another aspect, the disclosure provides a method of use of a compound having structural Formula (I) and/or Formula (II) in medical treatment and prevention.

In another aspect, the disclosure provides a method of use of a compound having structural Formula (I) and/or Formula (II) in medical treatment and prevention of pain (i.e, reducing pain for a subject in need thereof, including acute pain, chronic pain, inflammatory pain, neuropathic pain, cancer pain, and generalized pain disorder), cancer (e.g., pancreatic cancer, prostate cancer or metastasis, breast cancer, hepatocellular carcinoma, intrahepatic cholangiocarcinoma, liver cancer, ovarian cancer, thyroid cancer, lung (small cell and non-small cell) cancer, colorectal cancer, glioblastoma, spitz tumors, spitzoid melanomas, acute myelogenous leukemia, endometrial cancer, skin cancer, oral cancer, bone cancer, melanoma, gastric cancer, esophageal cancer, gastrointestinal cancer, brain cancer or human neuroblastoma, medulloblastoma, retinoblastoma, leukemia, lymphoma, malignant mesothelioma, bladder cancer, squamous cell carcinomas), atopic dermatitis, psoriasis, skin diseases, itch, liver fibrosis, liver cirrhosis, scabies, pityriasis, inflammatory bowel disease, inflammatory arthritis, asthma, human airway diseases, Chagas' disease, parasitic diseases, Alzheimer's, restenosis, atherosclerosis, thrombosis, liver cirrhosis, liver fibrosis, Pulmonary Inflammatory Diseases, pulmonary sarcoidosis, bladder dysfunction or lower urinary tract dysfunction, Paget's disease, diabetic nephropathy, irritable bowel syndrome, radiation, schizophrenia, or a disease, disorder or injury relating to dysmyelination or demyelination or the disease or disorder associated with abnormal activities of TrkA protein kinases or fusions or mutations of TrkA (NTRK1) protein, with combination of (a) therapeutic effective amount of the compound as described above, or a salt, solvate, or ester, prodrug, or physiologically functional derivative thereof, and either (b1) an opioid analgesic or at least one analgesic agent that acts by a mechanism different from a Trk antagonist or, (b2) an existing or approved anti-cancer agent or chemotherapeutic or at least one existing or approved anti-cancer agent.

In another aspect, the disclosure provides a method for preparing a compound having structural Formula (I) and/or Formula (II) described above.

In another aspect, the disclosure provides a method for treating a disease, disorder, symptom, or condition associated with irregular TrkA activity, or fusion or mutation of TrkA protein or NTRK1 gene in a patient suffering therefrom, comprising administering to the patient a pharmaceutical composition, comprising a therapeutically effective amount of a compound having structural Formula (I) and/or Formula (II), wherein the pharmaceutical composition is formulated in a unit dosage form selected from the group consisting of: an oral unit dosage form (including powder, tablets, pills, pellets, capsules, powders, lozenges, granules, solutions, suspensions, emulsion, syrups, elixirs, sustained-release formulations, aerosols, sprays and caplet), an inhalational unit dosage form (including spray, aerosol, inhaler, neulizer, smoking and vaporizer), a parenteral unit dosage form (including intradermal, intramuscular, intraosseous, intraperitoneal, intravenous, epidural, intracardiac, intraocular, intraarticular, subcutaneous and intrathecal injection unit dosage forms), a topical unit dosage form (including cream, gel, liniment or balm, lotion or ointment, ear drops, eye drops, skin patch and vaginal rings), an intranasal unit dosage form, a suppository unit dosage form (including vaginal, douche, pessary, and rectal), an epidural unit dosage form, a sublingual unit dosage form (including lozenge and troche), and an intracerebral unit dosage form.

In another aspect, the disclosure provides a method for treating a disease, disorder, symptom, or condition associated with irregular TrkA activity, or fusion or mutation of TrkA protein or NTRK1 gene in a patient suffering therefrom, comprising administering to the patient a pharmaceutical composition, comprising a therapeutically effective amount of a compound having structural Formula (I) and/or Formula (II), wherein the pharmaceutical composition is formulated in an oral unit dosage form comprising from about 0.02 mg of the compound per kg of body weight to about 60 mg of the compound per kg of body weight.

In another aspect, the disclosure provides a method for treating a disease, disorder, symptom, or condition associated with irregular TrkA activity, or fusion or mutation of TrkA protein or NTRK1 gene in a patient suffering therefrom, comprising administering to the patient a pharmaceutical composition, comprising a therapeutically effective amount of a compound having structural Formula (I) and/or Formula (II), wherein the pharmaceutical composition is formulated in an intravenous unit dosage form comprising from about 0.002 mg of the compound per kg of body weight to about 60 mg of the compound per kg of body weight.

In another aspect, the disclosure provides a method for treating a disease, disorder, symptom, or condition associated with irregular TrkA activity, or fusion or mutation of TrkA protein or NTRK1 gene in a patient suffering therefrom, comprising administering to the patient a pharmaceutical composition, comprising a therapeutically effective amount of a compound having structural Formula (I) and/or Formula (II), wherein the pharmaceutical composition is formulated in an intranasal unit dosage form comprising from about 0.002 mg of the compound per kg of body weight to about 6 mg of the compound per kg of body weight.

In another aspect, the disclosure provides a method for treating a disease, disorder, symptom, or condition associated with irregular TrkA activity, or fusion or mutation of TrkA protein or NTRK1 gene in a patient suffering therefrom, comprising administering to the patient a pharmaceutical composition, comprising a therapeutically effective amount of a compound having structural Formula (I) and/or Formula (II), wherein the pharmaceutical composition is formulated in a suppository unit dosage form comprising from about 0.001 mg of the compound per kg of body weight to about 50 mg of the compound per kg of body weight and comprise active ingredient in the range of about 0.5% to about 10% by weight.

In another aspect, the disclosure provides a method for treating a disease, disorder, symptom, or condition associated with irregular TrkA activity, or fusion or mutation of TrkA protein or NTRK1 gene in a patient suffering therefrom, comprising administering to the patient a pharmaceutical composition, comprising a therapeutically effective amount of a compound having structural Formula (I) and/or Formula (II), wherein the pharmaceutical composition is formulated in a unit dosage form selected from the group consisting of: a parenteral unit dosage form (including intradermal, intramuscular, intraosseous, intraperitoneal, intravenous, epidural, intracardiac, intraocular, intra-articular, subcutaneous and intrathecal injection unit dosage forms), a topical unit dosage form (including cream, gel, liniment or balm, lotion or ointment, ear drops, eye drops, skin patch and vaginal rings), an intranasal unit dosage form, a suppository unit dosage form (including vaginal, douche, pessary, and rectal), an epidural unit dosage form, a sublingual unit dosage form (including lozenge and troche), and an intracerebral unit dosage form, an intradermal unit dosage form, an intramuscular unit dosage form, an intraperitoneal unit dosage form, a subcutaneous unit dosage form, an epidural unit dosage form, a sublingual unit dosage form, and an intracerebral unit dosage form, wherein said unit dosage forms comprise from about 0.001 mg of the compound per kg of body weight to about 60 mg of the compound per kg of body weight.

5. DETAILED DESCRIPTION OF THE DISCLOSURE

The present disclosure relates to novel synthetic small molecules that act as inhibitors and/or antagonists of the members of Trk family protein kinases, in particularly the NGF receptor, TrkA.

5.1 Definitions

Terms used in the claims and specification are defined as set forth below unless otherwise specified.

The term "a compound of the present disclosure", "the compound of the present disclosure", "compounds of the present disclosure", or "the present compounds" refers to one or more compounds encompassed by the structural formulae and/or any subgeneric formulae disclosed herein and includes any specific compounds within these generic formula whose structure is disclosed herein. Compounds of the disclosure may contain one or more chiral centers and/or double bonds and therefore, may exist as stereoisomers, such as double-bond isomers (i.e., geometric isomers), the racemic mixtures, enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. The compounds of the disclosure may also exist in several tautomeric forms. Accordingly, the chemical structures depicted herein encompass all possible tautomeric forms of the illustrated compounds. Compounds also include isotopically labeled compounds where one or more atoms have an atomic mass different from the atomic mass conventionally found in nature. Examples of isotopes that may be incorporated into the compounds include, but are not limited to, $^{2}H$, $^{3}H$, $^{13}C$, $^{14}C$, $^{15}N$, $^{17}O$, $^{18}O$, etc. Compounds may exist in unsolvated forms as well as solvated forms, including hydrated forms and as N-oxides. In general, the salt, hydrated, solvated, and N-oxide forms are within the scope of the present disclosure. Certain compounds of the present disclosure may exist in multiple crystalline forms or an amorphous form. In general, all physical forms are equivalent for the uses contemplated by the present disclosure and are intended to be within the scope of the present disclosure.

The term "physiologically functional derivative(s)" used herein refers to any physiologically tolerated derivative of a compound of the present disclosure, for example, an ester or prodrug, which, upon administration to a mammal, e.g., a human, are transformed directly or indirectly to a compound of formula (I) and/or formula (II), or an active metabolite thereof. Physiologically functional derivatives include prodrugs of the compounds of the present disclosure. Examples of prodrug are described in H. Okada et al., *Chem. Pharm. Bull.* 1994, 42, 57-61. Such prodrugs can be metabolized in vivo to a compound of the disclosure. These prodrugs may themselves be active or not.

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl). Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent, refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is ($C_1$-$C_{20}$) alkyldiyl, more preferably, ($C_1$-$C_{10}$) alkyldiyl, most preferably, ($C_1$-$C_6$) alkyldiyl.

"Alkyleno" by itself or as part of another substituent, refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used.

"Acyl" by itself or as part of another substituent refers to a radical —C(O)$R^{200}$, where $R^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Amino" by itself or as part of another substituent refers to a radical —N$R^a R^b$, where $R^a$ and $R^b$ are independently hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein, or alternatively $R^a$ and $R^b$, taken together with the atoms to which they are bonded, form a cycloheteroalkyl ring. Representative examples include, but are not limited to —NH$_2$, —NHCH$_3$, —N(CH$_3$)$_2$, —NH-phenyl, —NH—CH$_2$-phenyl, pyrrolidine, and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 10 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or sp$^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_5$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Aryloxy," by itself or as part of another substituent, refers to a radical of the formula —O—$R^{201}$, where $R^{201}$ is aryl, substituted aryl, arylalkyl, or substituted arylalkyl.

"Aryloxycarbonyl," by itself or as part of another substituent, refers to a radical of the formula —C(O)—O—$R^{201}$, where $R^{201}$ is aryl, substituted aryl, arylalkyl, or substituted arylalkyl.

"Carboxy bioisostere," by itself or as part of another substituent, as used herein refers to a moiety that at physiological pH is expected to produce similar chemical or biological properties of a moiety of carboxylic acid at the same position of the compound. In certain embodiments, the carboxylate bioisostere is a moiety selected from the group consisting of —C(O)O$R^{11}$, —SO$_2 R^{11}$, —$C_{5-8}$ heterocycle, and —C(OH)(CF$_3$)$_2$; $R^{11}$ is independently selected from the group consisting of hydrogen, $C_{1-6}$ alkyl, NH$_2$, NHR$^a$, and NR$^a$C(=O)R wherein each said alkyl is independently optionally substituted, and wherein one carbon atom of said alkyl may be replaced with one heteroatom selected from the group consisting of nitrogen, oxygen, and sulfur; R each independently represents hydrogen, halogen, CN, NO$_2$, NH$_2$, or $C_{1-6}$ alkyl; $R^a$ each independently represents hydrogen or $C_{1-6}$ alkyl.

"Cycloalkyl" or "carbocyclyl" by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In some embodiments, a cycloalkyl group comprises from 3 to 10 ring atoms ($C_3$-$C_{10}$ cycloalkyl). In other embodiments, a cycloalkyl group comprises from 3 to 7 ring atoms ($C_3$-$C_7$ cycloalkyl).

"Cycloheteroalkyl" or "heterocyclyl" by itself or as part of another substituent, refers to a saturated or unsaturated cyclic alkyl radical in which one or more carbon atoms (and optionally any associated hydrogen atoms) are independently replaced with the same or different heteroatom. Typical heteroatoms to replace the carbon atom(s) include, but are not limited to, B, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, borolane, dioxaborolane, and the like. In some embodiments, the cycloheteroalkyl group comprises from 3 to 10 ring atoms (3-10 membered cycloheteroalkyl). In other embodiments, the cycloalkyl group comprise from 5 to 7 ring atoms (5-7 membered cycloheteroalkyl).

"Halogen" or "halo" by itself or as part of another substituent, refers to any of the elements fluorine, chlorine, bromine, iodine, and astatine, occupying group VIIA (17) of the periodic table.

A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom.

"Heteroalkyl, Heteroalkanyl, Heteroalkenyl, Heteroalkanyl, Heteroalkyldiyl and Heteroalkyleno" by themselves or as part of another substituent, refer to alkyl, alkanyl, alkenyl, alkynyl, alkyldiyl and alkyleno groups, respectively, in which one or more of the carbon atoms (and any associated hydrogen atoms) are each independently replaced with the same or different heteroatomic groups. Typical heteroatomic groups which can be included in these groups include, but are not limited to, —O—, —S—, —O—O—, —S—S—, —O—S—, —$NR^{203}R^{204}$—, =N—N=, —N=N—, —N=N—$NR^{205}R^{206}$, —$PR^{207}$—, —$P(O)_2$—, —$POR^{208}$—, —O—$P(O)_2$—, —SO—, —$SO_2$—, —$SnR^{209}R^{210}$—, —$BR^{211}R^{212}$, $BOR^{213}OR^{214}$ and the like, where $R^{203}$, $R^{204}$, $R^{205}$, $R^{206}$, $R^{207}$, $R^{208}$, $R^{209}$, $R^{210}$, $R^{211}$, $R^{212}$, $R^{213}$ and $R^{214}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, furopyridine, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Heteroaryloxy," by itself or as part of another substituent, refers to a radical of the formula —O—$R^{201}$, where $R^{201}$ is heteroaryl, substituted heteroaryl, heteroarylalkyl, or substituted heteroarylalkyl.

"Heteroaryloxycarbonyl," by itself or as part of another substituent, refers to a radical of the formula —C(O)—O—$R^{201}$, where $R^{201}$ is heteroaryl, substituted heteroaryl, heteroarylalkyl, or substituted heteroarylalkyl.

"Modulating" refers to adjusting, varying, or changing. As used herein, modulation of calcium ion channel includes antagonizing, agonizing, or partially antagonizing. That is, the compounds of the present disclosure may act as antagonists, agonists, or partial antagonists of the calcium ion channel activity.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, B, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Patient" or "subject" includes, but is not limited to animals such as, for example, mammals. Preferably, the patient is a human.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute, i.e., a compound of the present disclosure), or an aggregate that consists of a solute ion or molecule (the compound of the present disclosure) with one or more solvent molecules.

"Pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Prodrug or softdrug" refers to a precursor of a pharmaceutically active compound wherein the precursor itself may or may not be pharmaceutically active but, upon administration, will be converted, either metabolically or otherwise, into the pharmaceutically active compound or drug of interest. For example, prodrug or softdrug is an ester or an ether form of a pharmaceutically active compound. Several prodrugs have been prepared and disclosed for a variety of pharmaceuticals. See, for example, Bundgaard, H. and Moss, J., J. Pharm. Sci. 78: 122-126 (1989). Thus, one of ordinary skill in the art knows how to prepare these precursors, prodrugs or softdrugs with commonly employed techniques of organic synthesis.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halogen, —$O^-$, =O, —$OR^b$, —$SR^b$, —S—, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O$—, —$S(O)_2OR^b$, —$OS(O)_2R^b$, —$OS(O)_2O$—, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O$—, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O$—, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, substituted alkyl, arylalkyl, alkyldiyl, substituted alkyldiyl, aryl, substituted aryl, arylalkyl, substituted arylalkyl, heteroalkyl, substituted heteroalkyl, heteroalkyldiyl, substituted heteroalkyldiyl, heteroaryl, substituted heteroaryl, heteroarylalkyl substituted heteroarylalkyl; each $R^b$ is independently hydrogen or $R^a$; and each $R^c$ is independently $R^b$ or alternatively, the two $R^c$s are taken together with the nitrogen atom to which they are bonded form a cycloheteroalkyl ring which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halogen, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O$—, —$S(O)_2OR^b$, —$OS(O)_2R^b$, —$OS(O)_2O$—, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O$—, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —S—, —$NR^cR^c$, trihalomethyl, —$CF_3$, —CN, —NO, —$NO_2$, —$S(O)_2R^b$, —$S(O)_2O$—, —$S(O)_2OR^b$, —$OS(O)_2R^b$, —$OS(O)_2O$—, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art. The substituents used to substitute a specified group can be further substituted, typically with one or more of the same or different groups selected from the various groups specified above. The term "optionally substituted", when used with a specific group, means the specific group can be substituted or unsubstituted. For example, an optionally substituted alkyl denotes a substituted alkyl or unsubstituted alkyl.

"Treating", "treat" or "treatment" of any disease or disorder refers, in some embodiments, to ameliorating or preventing the disease or disorder (i.e., arresting, preventing, holding or reducing the development of the disease or at least one of the clinical symptoms thereof). In other embodiments "treating", "treat" or "treatment" refers to ameliorating at least one physical parameter, which may not be discernible by the patient. In yet other embodiments, "treating", "treat" or "treatment" refers to inhibiting, or holding or preventing the progress of, the disease or disorder, either physically, (e.g., stabilization of a discernible symptom), physiologically, (e.g., stabilization of a physical parameter) or both. In yet other embodiments, "treating", "treat" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

"Vehicle" refers to a diluent, adjuvant, excipient or carrier with which a compound is administered.

Reference will now be made in detail to preferred embodiments of the disclosure. While the disclosure will be described in conjunction with the preferred embodiments, it will be understood that it is not intended to limit the disclosure to those preferred embodiments. To the contrary, it is intended to cover alternatives, modifications, and equivalents as may be included within the spirit and scope of the disclosure as defined by the appended claims.

The term "receptor" refers to a molecule or complex of molecules, typically (although not necessarily) a protein(s), that is specifically bound by one or more particular ligands. The receptor is said to be a receptor for such ligand(s). Ligand-receptor binding, in many instances, induces one or more biological responses. A "modulator" of a polypeptide is either an inhibitor or an enhancer of an action or function of the polypeptide. Similarly, a "modulator" of a signaling pathway is an inhibitor or enhancer of at least one function mediated by the signaling pathway. Aspects of modulators are defined below with respect to polypeptides; however, those of skill in the art readily appreciate that these definitions also apply to signaling pathways.

A "non-selective" modulator of a polypeptide is an agent that modulates other members of the same family of polypeptides at the concentrations typically employed for modulation of the particular polypeptide.

A "selective" modulator of a polypeptide significantly modulates the particular polypeptide at a concentration at which other members of the same family of polypeptides are not significantly modulated.

A modulator "acts directly on" a polypeptide when the modulator exerts its action by interacting directly with the polypeptide.

A modulator "acts indirectly on" a polypeptide when the modulator exerts its action by interacting with a molecule other than the polypeptide, which interaction results in modulation of an action or function of the polypeptide.

An "inhibitor" or "antagonist" of a polypeptide is an agent that reduces, by any mechanism, any action or function of the polypeptide, as compared to that observed in the absence (or presence of a smaller amount) of the agent. An inhibitor of a polypeptide can affect: (1) the expression, mRNA stability, protein trafficking, modification (e.g., phosphorylation), or degradation of a polypeptide, or (2) one or more of the normal action or functions of the polypeptide. An inhibitor of a polypeptide can be non-selective or selective. Preferred inhibitors (antagonists) are generally small molecules that act directly on, and are selective for, the target polypeptide.

A "reversible" inhibitor is one whose effects can be reversed (i.e., one that does not irreversibly inactivate the target polypeptide).

A "competitive" inhibitor of a polypeptide is one that competes for binding to the polypeptide with another component required for polypeptide function. For example, TrkA function requires the binding of ATP and substrate. Accordingly, a competitive inhibitor of TrkA can act, for example, by binding at the ATP or substrate binding sites. This inhibition is generally reversible by increasing the concentration of ATP or substrate to the reaction mixture. Such an inhibitor is said to inhibit TrkA competitively with respect to ATP or substrate, respectively.

A "non-competitive" inhibitor of a polypeptide generally binds the polypeptide at a site other than the binding site of another component required for polypeptide function. This inhibition cannot be reversed by increasing the concentration of component(s) required for polypeptide function.

As used herein, an "allosteric modulator" of an polypeptide, typically an enzyme or receptor, is a modulator that binds at a location other than the active site of the target polypeptide, altering activity by inducing an allosteric change in the shape of the target polypeptide.

The terms "polypeptide" and "protein" are used interchangeably herein to refer a polymer of amino acids, and unless otherwise limited, include atypical amino acids that can function in a similar manner to naturally occurring amino acids.

The term "specific binding" is defined herein as the preferential binding of binding partners to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

The phrases "an effective amount" and "an amount sufficient to" refer to amounts of a biologically active agent that produce an intended biological activity.

The term "co-administer" or "co-administering" when used in reference to the administration of Trk (i.e., TrkA) antagonists and other agents indicates that the antagonist and other agent(s) are administered in a coordinated fashion so that there is at least some chronological overlap in their physiological activity on the subject. Thus, a TrkA antagonist can be administered simultaneously and/or sequentially with another agent. In sequential administration, there may even be some substantial delay (e.g., minutes or even hours or days) before administration of the second agent as long as the first administered agent is exerting some physiological effect on the organism when the second administered agent is administered or becomes active in the subject.

The term "reducing pain", as used herein, refers to decreasing the level of pain a subject perceives relative to the level of pain the subject would have perceived were it not for the intervention. Where the subject is a person, the level of pain the person perceives can be assessed by asking him or her to describe the pain or compare it to other painful experiences. Alternatively, pain levels can be determined by measuring the subject's physical responses to the pain, such as the release of stress-related factors or the activity of pain-transducing nerves in the peripheral nervous system or the CNS. One can also determine pain levels by measuring the amount of a well-characterized analgesic required for a person to report that no pain is present or for a subject to stop exhibiting symptoms of pain. A reduction in pain can also be measured as an increase in the threshold at which a subject experiences a given stimulus as painful. In certain embodiments, a reduction in pain is achieved by decreasing "hyperalgesia," the heightened sensitivity to a noxious stimulus, and such inhibition can occur without impairing "nociception," the subject's normal sensitivity to a "noxious" stimulus. The term "pain", as used herein, refers also to, for examples, acute pain, chronic pain, inflammatory pain, neuropathic pain, and generalized pain disorder.

As used with reference to pain reduction, "a subject in need thereof" refers to an animal or person, preferably a person, expected to experience pain in the near future. Such animal or person may have an ongoing condition that is causing pain currently and is likely to continue to cause pain. Alternatively, the animal or person has been, is, or will be enduring a procedure or event that usually has painful consequences. Chronic painful conditions such as diabetic neuropathic hyperalgesia and collagen vascular diseases are examples of the first type; dental work, particularly that accompanied by inflammation or nerve damage, and toxin exposure (including exposure to chemotherapeutic agents) are examples of the latter type.

"Inflammatory pain" refers to pain arising from inflammation. Inflammatory pain often manifests as increased sensitivity to mechanical stimuli (mechanical hyperalgesia or tenderness). For examples, inflammatory pain is due to a condition selected from the group consisting of: burn, sunburn, arthritis, osteoarthritis, colitis, carditis, dermatitis, myositis, neuritis, mucositis, urethritis, cystitis, gastritis, pneumonitis, and collagen vascular disease.

"Neuropathic pain" refers to pain arising from conditions or events that result in nerve damage. "Neuropathy" refers to a disease process resulting in damage to nerves. "Causalgia" denotes a state of chronic pain following nerve injury. "Allodynia" refers to a condition in which a person experiences pain in response to a normally nonpainful stimulus, such as a gentle touch. For examples, neuropathic pain is due to a condition selected from the group consisting of: causalgia, diabetes, diabetic peripheral neuropathy, collagen vascular disease, trigeminal neuralgia, spinal cord injury, brain stem injury, thalamic pain syndrome, complex regional pain syndrome type I/reflex sympathetic dystrophy, Fabry's syndrome, small fiber neuropathy, cancer, cancer chemotherapy, chronic alcoholism, stroke, abscess, demyelinating disease, viral infection, anti-viral therapy, AIDS, and AIDS therapy. Neuropathic pain is due to an agent selected from the group consisting of: trauma, surgery, amputation, toxin, and chemotherapy.

As used herein, the term "generalized pain disorder" refers to a group of idiopathic pain syndromes (e.g., fibromyalgia, irritable bowel syndrome, and temporomandibular disorders), for which the pathogenic mechanism is currently unknown, characterized by diffuse or generalized pain, and for which a diagnosis of inflammation or neuropathy as the direct cause of pain is excluded.

An "analgesic agent" refers to a molecule or combination of molecules that causes a reduction in pain.

The difference between "acute" and "chronic" pain is one of timing: acute pain is experienced soon (e.g., generally within about 48 hours, more typically within about 24 hours, and most typically within about 12 hours) after the occurrence of the event (such as inflammation or nerve injury) that led to such pain. By contrast, there is a significant time lag between the experience of chronic pain and the occurrence of the event that led to such pain. Such time lag is generally at least about 48 hours after such event, more typically at least about 96 hours after such event, and most typically at least about one week after such event.

The term "maladaptive substance use" refers to the use of any substance that results in adverse consequences for the user that outweigh any benefits derived from the substance. Substances that are used in a maladaptive manner are generally consumed or administered (usually self-administered) to the body, by any route of administration, to produce an effect on the body that the user generally experiences as pleasurable. The substance can be a single substance (cocaine, for example) or a type of substance (e.g., food, in general). The adverse consequences can include, for example, adverse effects on health, the ability to care for oneself, the ability to form and maintain human relationships, and/or the ability to work. The adverse consequences are generally significant enough that the user would like to control, reduce, or end substance use or, alternatively, the user's family members and/or friends would like to see the user control, reduce, or end substance use. Maladaptive substance use can include uncontrollable craving for the substance; substance dependence, including psychological and/or physical dependence; and maladaptive substance use; as well as any of the individual symptoms of substance dependence and/or abuse listed below.

The term "neurosteroid" refers to a class of steroids, the natural forms of which are produced by cells of the central or peripheral nervous systems, independently of the steroidogenic activity of the endocrine glands. Neurosteroids are derived from cholesterol, and examples of neurosteroids include $3\alpha,5\alpha$-tetrahydroprogesterone, $3\alpha,5\beta$-tetrahydroprogesterone, and $3\alpha,5\alpha$-tetrahydrodeoxycorticosterone. For examples, ganaxalone and alphaxalone.

A "benzodiazepine" is referred to an agent selected from the group consisting of: alprazolam, chlordiazepoxide, chlordiazepoxide hydrochloride, chlormezanone, clobazam, clonazepam, clorazepate dipotassium, diazepam, droperidol, estazolam, fentanyl citrate, flurazepam hydrochloride, halazepam, lorazepam, midazolam hydrochloride, oxazepam, prazepam, quazepam, temazepam, and triazolam.

A "barbiturate" referred to an agent selected from the group consisting of: amobarbital, amobarbital sodium, aprobarbital, butabarbital sodium, hexobarbital sodium, mephobarbital, metharbital, methohexital sodium, pentobarbital, pentobarbital sodium, phenobarbital, phenobarbital sodium, secobarbital, secobarbital sodium, talbutal, thiamylal sodium, and thiopental sodium.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure and a pharmaceutically acceptable carrier. By "pharmaceutically acceptable" it is meant the carrier, diluent or excipient must be compatible with the other ingredients of the formulation and not deleterious to the recipient thereof.

The term "cancer" refers to or describes the physiological condition in mammals that is typically characterized by unregulated cell growth. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ALL), squamous cell carcinoma, lung cancer (for examples, small-cell lung cancer, and non-small cell lung cancer), glioma, gastrointestinal cancer, renal cancer, ovarian cancer, liver cancer (for examples, hepatocellular carcinoma, fibrolamellar carcinoma, cholangiocarcinoma, angiosarcoma, hepatoblastoma, haemangioma, hepatic adenomas, and focal nodular hyperplasia, and metastasis liver cancer), colorectal cancer, endometrial cancer, kidney cancer, prostate cancer, thyroid cancer, neuroblastoma, pancreatic cancer (for examples, adenocarcinoma, islet cell carcinoma, pancreaticoblastoma, isolated sarcomas and lymphomas, pseudopapillary neoplasms, ampullary cancer, exocrine tumors, neuroendocrine tumors and endocrine tumors), glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, metastasis, acute myelogenous leukemia (AML), and chronic lymphocytic leukemia (CML).

It is to be understood that this disclosure is not limited to particular methods, reagents, compounds, compositions, or biological systems, which can, of course, vary. It is also to be understood that the terminology used herein is for the purpose of describing particular aspects only, and is not intended to be limiting. As used in this specification and the appended claims, the singular forms "a", "an", and "the" include plural referents unless the content clearly dictates otherwise. Thus, for example, reference to "a compound" includes a combination of two or more compounds or molecules, and the like.

5.2 Compounds

In one aspect, the present disclosure provides compounds having structural Formula (I),

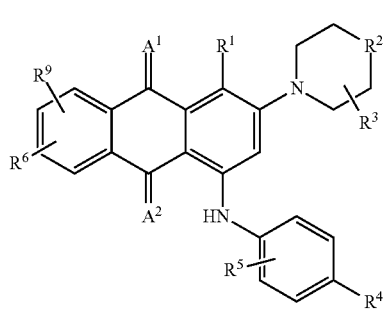

(I)

or a salt, solvate, ester, or prodrug thereof;

wherein:
$A^1$ and $A^2$ are independently oxygen or sulfur;
$R^1$ represents $NH_2$ or $R^7$;
$R^2$ represents $NR^7$ or $CR^7R^{10}$;
$R^3$, $R^5$, $R^6$, and $R^9$ are independently $R^7$;
or alternatively, $R^6$ and $R^9$, taken together with the atom(s) to which they are attached, form a 3 to 6 membered optionally substituted heteroclcylic group containing one or more heteroatoms selected from the group consisting of nitrogen, oxygen, and sulfur;
$R^4$ represents halogen, CN, $NO_2$, $CF_3$, $-(CHR)_nCOOR^{11}$, $-(CHR)_nSO_2R^{11}$, $C_{1-4}$ haloalkyl, $-OC_{1-4}$-haloalkyl, $C_{2-6}$ alkyl, $C_{2-6}$ alkenyl, $C_{2-6}$ alkynyl, $-(CHR)_nC_{6-10}$ aryl, $-(CHR)_nC_{5-8}$ heterocycle, $-(CHR)_nC_{3-8}$ cycloalkyl, $-O-C_{6-10}$ aryl, $-O-C_{5-10}$ heterocycle, $-(CHR)_nC(O)CF_3$, $-(CHR)_nC(OH)(CF_3)_2$, $-(CH_2)_n$halogen, $-OR_{10}$, $-NR^{11}R^{12}$, $-NR^aCOR^{11}$, $-NR^aCOOR^{11}$, $-NR^aSO_2R^{11}$, $-NR^aCONR^{11}R^{12}$, $-COR^{11}$, tetrazole, $-(CHR)_n$tetrazole, $-S-C_{1-6}$ alkyl, or $-CONR^{11}R^{12}$, wherein each said alkyl, alkenyl, alkynyl, aryl, cycloalkyl and heterocycle is independently optionally substituted with 1 to 2 groups of $R^8$;
or alternatively, $R^4$ and $R^5$, taken together with the atom(s) to which they are attached, form a 3 to 6 membered optionally substituted heteroclcylic group containing one or more heteroatoms selected from the group consisting of nitrogen, oxygen, and sulfur;
$R^7$ and $R^{10}$ are independently selected from the group consisting of hydrogen, halogen, CN, $NH_2$, $NO_2$, $C_{1-4}$ haloalkyl, $-OC_{1-4}$ haloalkyl, $C_{1-6}$ alkyl, $C_{2-6}$ alkenyl, $C_{2-6}$ alkynyl, $-(CHR)_nC_{6-10}$ aryl, $-(CHR)_nC_{5-8}$ heterocycle, $-(CHR)_nC_{3-8}$ cycloalkyl, $-O-C_{6-10}$ aryl, $-O-C_{5-10}$ heterocycle, $-C(O)CF_3$, $-(CH_2)_n$halogen, $-(CHR)_n-(O)_n-C(=O)R^8$, $-(CHR)_n-(S)_n-C(=O)R^8$, $-OR^a$, $-NR^{11}R^{12}$, $-NR^aCOR^{11}$, $-NR^aCOOR^a$, $-NR^aSO_2R$, $-NR^aCONR^{11}R^{12}$, $-COR^a$, $-(CHR)_nCOOR^a$, $-S-C_{1-6}$ alkyl, and $-CONR^{11}R^{12}$, wherein each said alkyl, alkenyl, alkynyl, aryl, cycloalkyl and heterocycle is independently optionally substituted with 1 to 2 groups of $R^8$;
$R^{11}$ and $R^{12}$ are independently selected from the group consisting of hydrogen, $NR^aC(=O)R$, halogen, CN, $NH_2$, $NHR^a$, $NO_2$, $C_{1-4}$ haloalkyl, $-OC_{1-4}$ haloalkyl, $C_{1-6}$ alkyl, $C_{2-8}$ alkenyl, $-S-C_{1-6}$ alkyl, $-C(=O)-(O)_n-R^a$, $-(CHR)_n-(O)_n-C(=O)R^8$, $-(CHR)_n-(S)_n-C(=O)R^8$, $-OR^a$, $-(CHR)_nC_{3-10}$ cycloalkyl, $-(CHR)_nC_{6-10}$ aryl, $-(CHR)_nC_{5-10}$ heteroaryl, and $-(CHR)_nC_{5-10}$ heterocycle, wherein each said alkyl, alkenyl, cycloalkyl, aryl, heteroaryl and heterocycle is independently optionally substituted with 1 to 2 groups of $R^8$, and wherein one or more carbon atoms of said alkyl may be replaced with one or more heteroatoms selected from the group consisting of nitrogen, oxygen, and sulfur;
or alternatively, $R^{11}$ and $R^{12}$, taken together with the atom(s) to which they are attached, form a 3 to 6 membered optionally substituted heteroclcylic group containing one or more heteroatoms selected from the group consisting of nitrogen, oxygen, and sulfur; wherein the optional substituent is $R^8$; and
R each independently represents hydrogen, halogen, CN, $NO_2$, $NH_2$, or $C_{1-6}$ alkyl;
$R^a$ each independently represents hydrogen or $C_{1-6}$ alkyl;
$R^8$ each independently represents $C_{1-6}$ alkyl, halogen, CN, $NO_2$, $NH_2$, $NHR^a$, $SO_2R^{11}$, or $NR^aSO_2R^{11}$; and
n represents an integer from 0 to 3, i.e., 0, 1, 2, or 3;
with the following provisos:
when $R^2$ is $CH_2$, $R^4$ is not H or $CH_3$;
when $R^2$ is $NCH_2CH_2OH$, (a) $R^4$ is not H or $OCH_3$, or (b) $R^5$ is not $OCH_3$; and
when $R^2$ is $N(CH_3)$, $R^4$ is not H, $CH_3$, $OCH_3$, or F.

In one embodiment of formula (I), $R^1$ is selected from the group consisting of hydrogen, —$(CH_2)_n$halogen, —CN, —$CH_3$, $NH_2$, $NHR^a$, and —$C_{1-3}$ alkyl;

In one embodiment of formula (I), $R^4$ is selected from the group consisting of —$C(O)OR^{11}$, —$SO_2NHC(=O)CH_3$, —$C(CF_3)(CF_3)OH$, —$SO_2NH_2$, —$C(O)NR^{11}R^{12}$, —CN, —$CF_3$, —$NO_2$, —$C(O)CF_3$, —$(CH_2)_n$halogen,

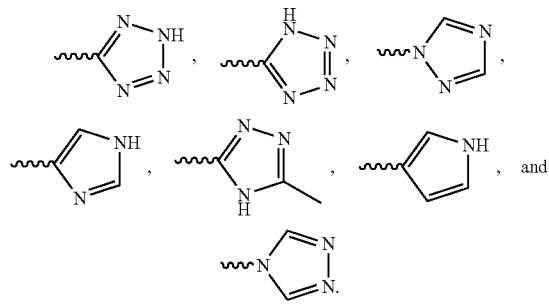

In one embodiment of formula (I), $R^3$, $R^5$, $R^6$, and $R^9$ are hydrogen.

In one embodiment of formula (I), $R^2$ is selected from the group consisting of

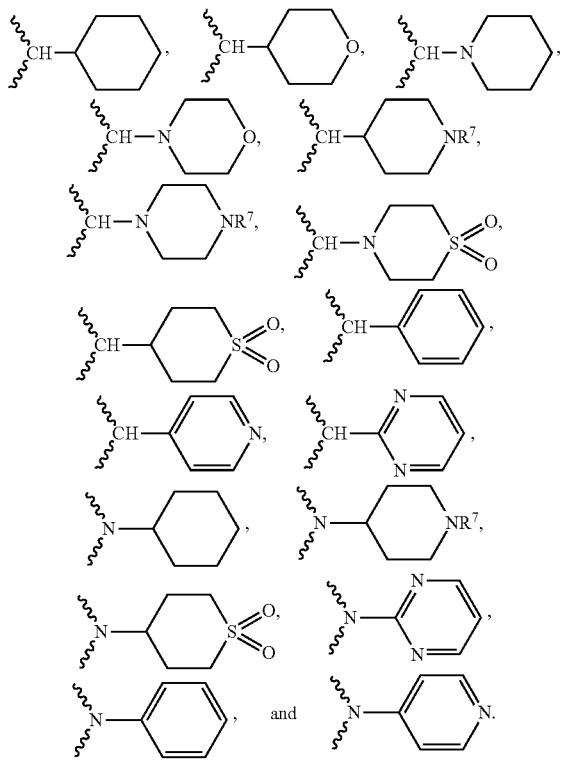

In one embodiment of formula (I), $A^1$ and $A^2$ are oxygen; $R^1$ represents $NH_2$; $R^2$ represents $NR^7$ or $CHR^7$; $R^3$, $R^5$, $R^6$, and $R^9$ are hydrogen; $R^7$ is $C_{5-8}$ heterocycle or $C_{3-8}$ cycloalkyl; and $R^4$ is selected from the group consisting of —$C(O)OR^{11}$, —$SO_2NHC(=O)CH_3$, —$C(CF_3)(CF_3)OH$, —$SO_2NH_2$, —$C(O)NR^{11}R^{12}$, —CN, —$CF_3$, —$NO_2$, —$C(O)CF_3$, —$(CH_2)_n$halogen,

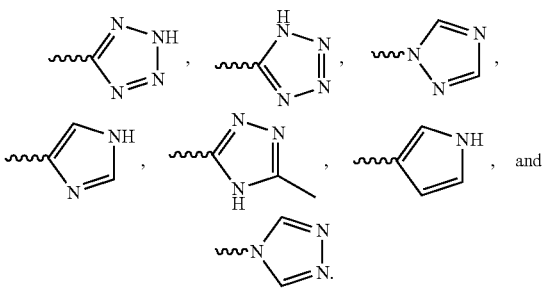

In one embodiment of $R^2$, it is selected from the group consisting of

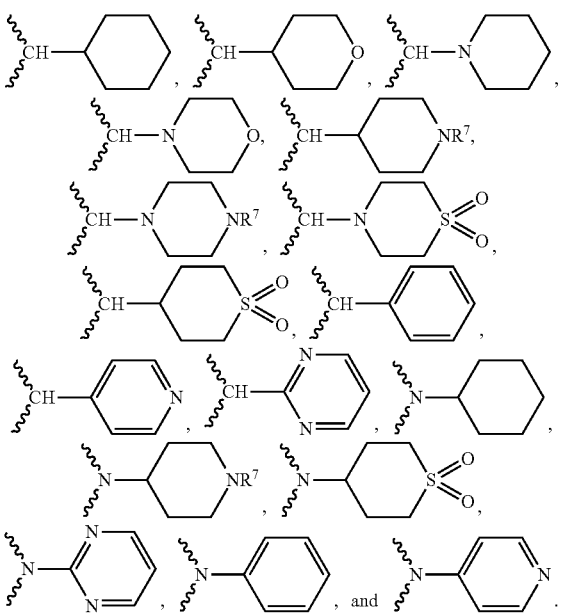

In another aspect, the present disclosure provides compounds having structural Formula (II):

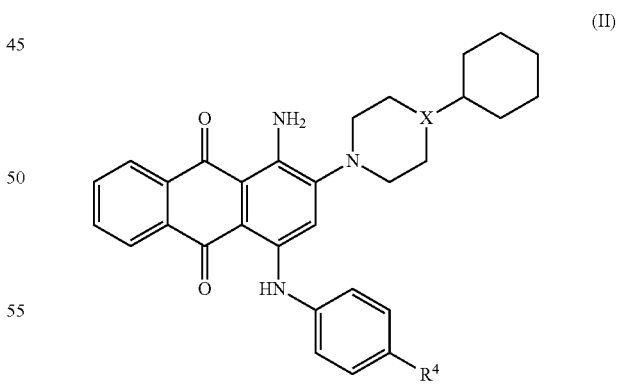

(II)

or a salt, solvate, ester, or prodrug thereof;
wherein:
X represents N or CH;
$R^4$ represents carboxy bioisostere selected from —$(CHR)_n COOR^{11}$, —$(CHR)_n SO_2 R^{11}$, —$(CHR)_n C_{5-8}$ heterocycle, or —$(CHR)_n C(OH)(CF_3)_2$, wherein each said heterocycle is independently optionally substituted with 1 to 2 groups of $R^8$;

R[11] is independently selected from the group consisting of hydrogen, $C_{1-6}$ alkyl, $NH_2$, $NHR^a$, and $NR^aC(=O)R$ wherein each said alkyl is independently optionally substituted with 1 to 2 groups of $R^8$, and wherein one carbon atom of said alkyl may be replaced with one heteroatom selected from the group consisting of nitrogen, oxygen, and sulfur;

$R^8$ each independently represents $C_{1-6}$ alkyl, halogen, CN, $NO_2$, $NH_2$, $NHR^a$, $SO_2R^{11}$, or $NR^aSO_2R_{11}$;

R each independently represents hydrogen, halogen, CN, $NO_2$, $NH_2$, or $C_{1-6}$ alkyl;

$R^a$ each independently represents hydrogen or $C_{1-6}$ alkyl; and n represents 0.

In one embodiment of formula (II), X represents N.

In one embodiment of formula (II), $R^4$ represents —$COOR^{11}$, wherein $R^{11}$ is hydrogen. In one embodiment of formula (II), $R^4$ represents —$COOR^{11}$, wherein $R^{11}$ is $C_{1-6}$ alkyl. In some embodiments of formula (II), $R^4$ represents —$COOR^{11}$, wherein $R^{11}$ is $C_{1-6}$ alkyl where one carbon atom of said $C_{1-6}$ alkyl is replaced with one nitrogen atom.

In one embodiment of formula (II), X represents N and $R^4$ represents —$COOR^{11}$, wherein $R^{11}$ is hydrogen.

In another embodiment of formula (II), $R^4$ represents —$SO_2R^{11}$, wherein $R^{11}$ is $NH_2$ or $NR^aC(=O)R$. In some embodiments of formula (II), $R^4$ represents —$SO_2R^{11}$, wherein $R^{11}$ is $NHC(=O)R$ and wherein R is $C_{1-6}$ alkyl.

In one embodiment of formula (II), $R^4$ represents $C_5$ heterocycle, wherein the heterocycle is a tetrazole.

In certain specific embodiments, the compounds of formula (I) and/or formula (II) are selected from the group consisting of

TABLE 1

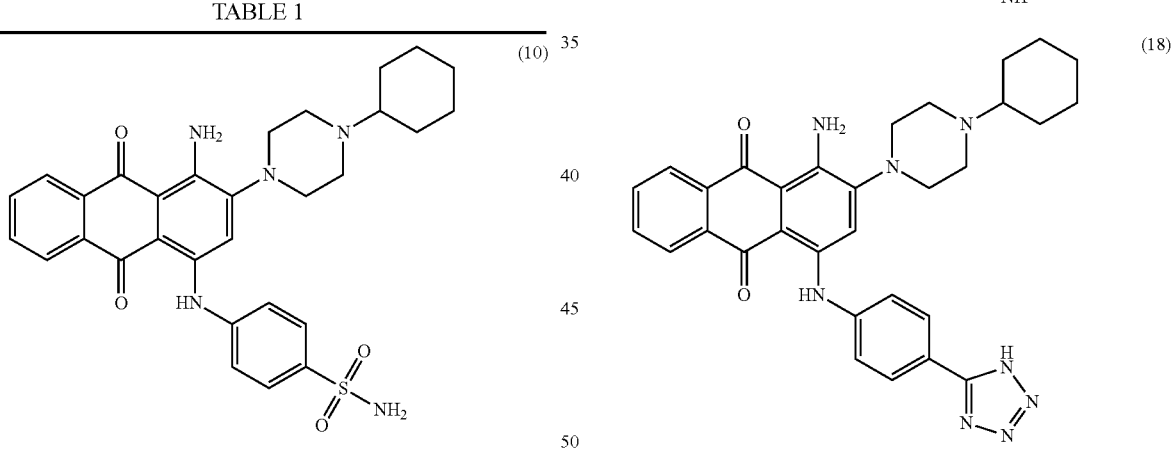

TABLE 1-continued

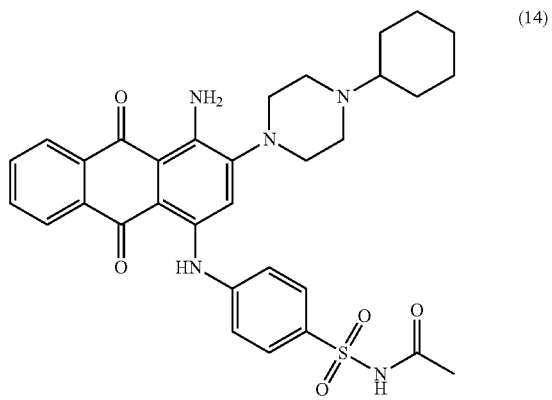

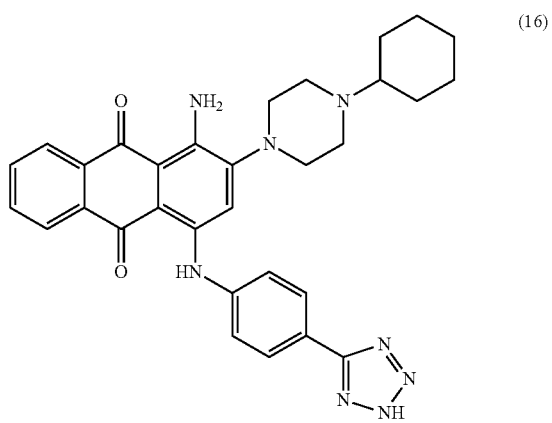

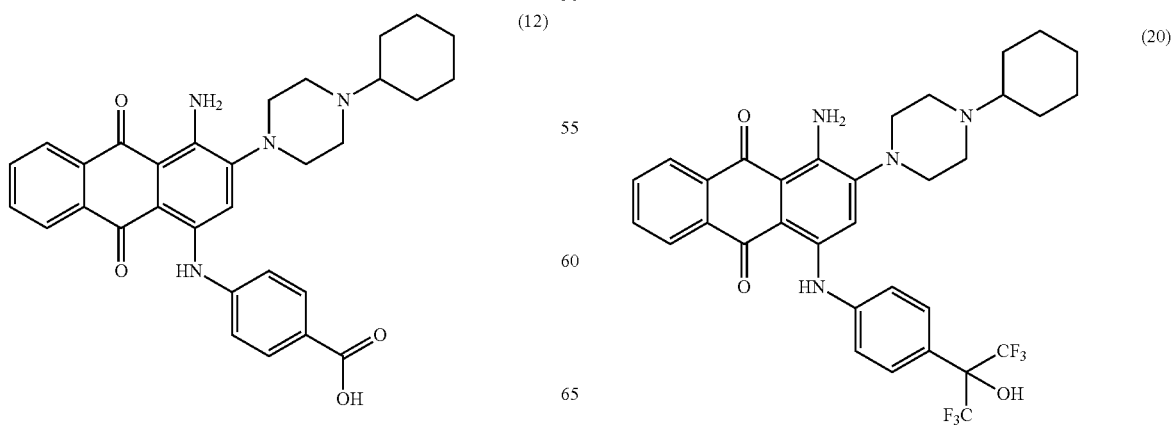

TABLE 1-continued
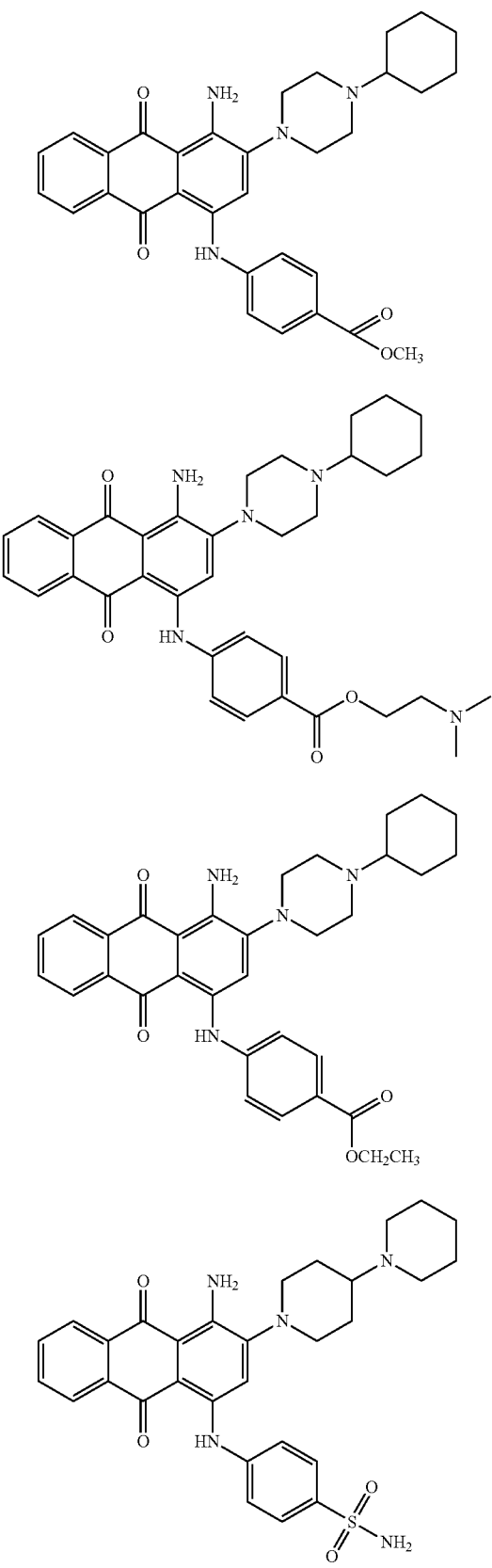
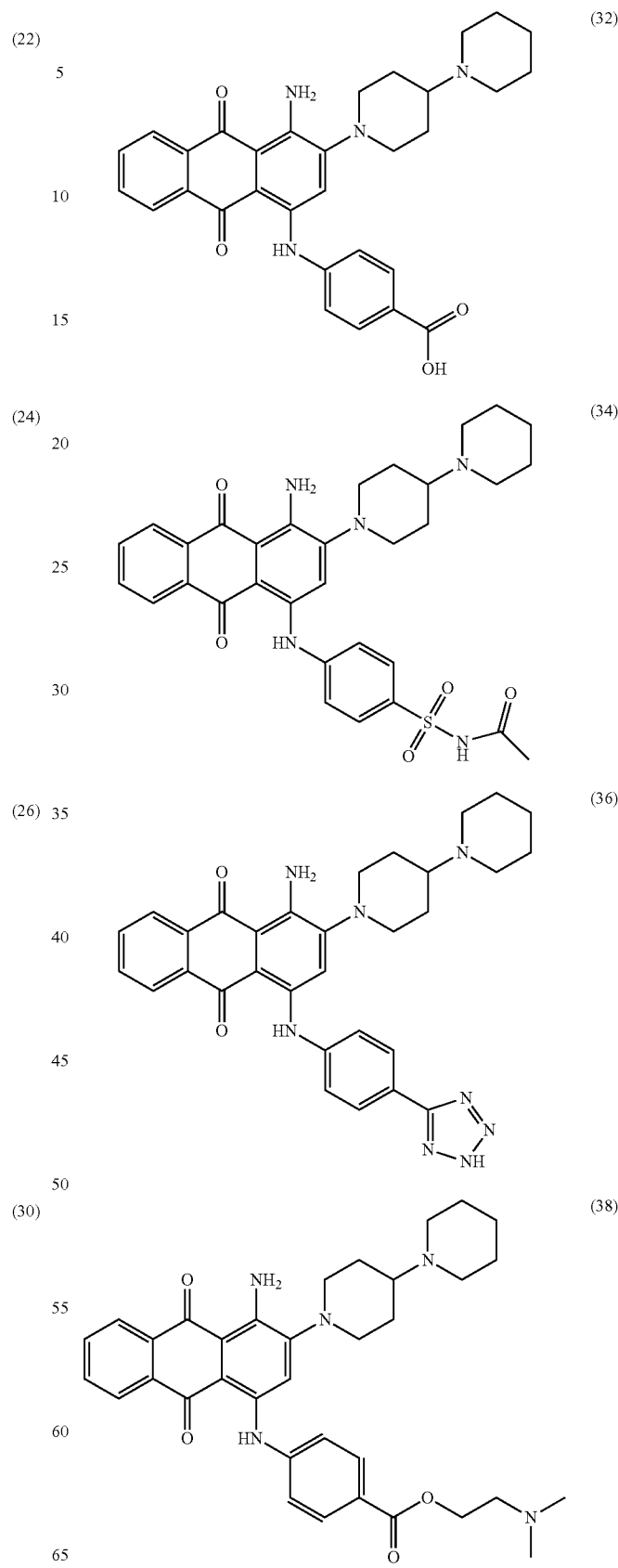

TABLE 1-continued

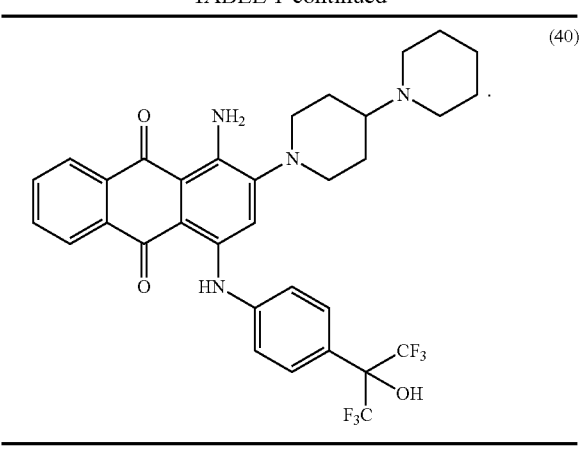

(40)

Compounds listed in Table 1 may also be represented by their chemical names as follows:

ID IUPAC Name 10 4-{[4-amino-3-(4-cyclohexylpiperazin-1-yl)-9,10-dioxo-9,10-dihydroanthracen-1-yl]amino}benzenesulfonamide;

12 4-{[4-amino-3-(4-cyclohexylpiperazin-1-yl)-9,10-dioxo-9,10-dihydroanthracen-1-yl]amino}benzoic acid;

14 N-[(4-{[4-amino-3-(4-cyclohexylpiperazin-1-yl)-9,10-dioxo-9,10-dihydroanthracen-1-yl]amino}phenyl)sulfonyl]acetamide;

16 1-amino-2-(4-cyclohexylpiperazin-1-yl)-4-{[4-(2H-tetrazol-5-yl)phenyl]amino}anthracene-9,10-dione;

18 1-amino-2-(4-cyclohexylpiperazin-1-yl)-4-{[4-(1H-tetrazol-5-yl)phenyl]amino}anthracene-9,10-dione;

20 1-amino-2-(4-cyclohexylpiperazin-1-yl)-4-{[4-(1,1,1,3,3,3-hexafluoro-2-hydroxypropan-2-yl)phenyl]amino}anthracene-9,10-dione;

22 methyl 4-{[4-amino-3-(4-cyclohexylpiperazin-1-yl)-9,10-dioxo-9,10-dihydroanthracen-1-yl]amino}benzoate;

24 2-(dimethylamino)ethyl 4-{[4-amino-3-(4-cyclohexylpiperazin-1-yl)-9,10-dioxo-9,10-dihydroanthracen-1-yl]amino}benzoate;

26 ethyl 4-{[4-amino-3-(4-cyclohexylpiperazin-1-yl)-9,10-dioxo-9,10-dihydroanthracen-1-yl]amino}benzoate;

30 4-{[4-amino-3-(1,4'-bipiperidin-1'-yl)-9,10-dioxo-9,10-dihydroanthracen-1-yl]amino}benzenesulfonamide;

32 4-{[4-amino-3-(1,4'-bipiperidin-1'-yl)-9,10-dioxo-9,10-dihydroanthracen-1-yl]amino}benzoic acid;

34 N-[(4-{[4-amino-3-(1,4'-bipiperidin-1'-yl)-9,10-dioxo-9,10-dihydroanthracen-1-yl]amino}phenyl)sulfonyl]acetamide;

36 1-amino-2-(1,4'-bipiperidin-1'-yl)-4-{[4-(2H-tetrazol-5-yl)phenyl]amino}anthracene-9,10-dione;

38 2-(dimethylamino)ethyl 4-{[4-amino-3-(1,4'-bipiperidin-1'-yl)-9,10-dioxo-9,10-dihydroanthracen-1-yl]amino}benzoate; and 40 1-amino-2-(1,4'-bipiperidin-1'-yl)-4-{[4-(1,1,1,3,3,3-hexafluoro-2-hydroxypropan-2-yl)phenyl]amino}anthracene-9,10-dione.

In one embodiment of the present disclosure, the compounds listed in Table 2 based on Formula (III) are excluded.

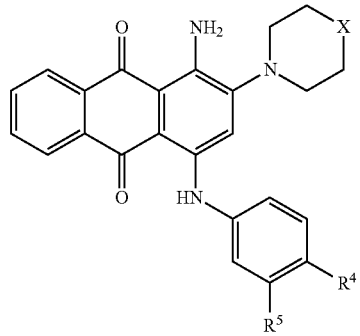

(III)

TABLE 2

| Compound ID | X | $R^4$ | $R^5$ |
|---|---|---|---|
| E1 | $CH_2$ | H | H |
| E2 | $CH_2$ | $CH_3$ | H |
| E3 | $NCH_3$ | H | H |
| E4 | $NCH_3$ | $CH_3$ | H |
| E5 | $NCH_3$ | F | H |
| E6 | $NCH_3$ | $OCH_3$ | H |
| E7 | $NCH_3$ | H | F |
| E8 | $NCH_3$ | H | $OCH_3$ |
| E9 | $NCH_2CH_2OH$ | H | H |
| E10 | $NCH_2CH_2OH$ | $OCH_3$ | H |
| E11 | $NCH_2CH_2OH$ | H | $OCH_3$ |

5.3 Synthesis of the Compounds

Several methods for preparing the compounds of this disclosure are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; BuLi: butyllithium; Piv: pivaloyl; Ac: acetyl; THF: tetrahydrofuran; DMSO: dimethylsulfoxide; EDC: N-(3-Dimethylaminopropyl)-N'-ethylcarbodiimide; Boc: tert-butyloxy carbonyl; $Et_3N$: triethylamine; DCM: dichloromethane; DCE: dichloroethane; DME: dimethoxyethane; DBA: diethylamine; DAST: diethylaminosulfur trifluoride; EtMgBr: ethylamgnesium bromide; BSA: bovine serum albumin; TFA: trifluoracetic acid; DMF: N,N-dimethylformamide; $SOCl_2$: thionyl chloride; CDI: carbonyl diimidazole; rt: room temperature; HPLC: high performance liquid chromatography; TLC: thin-layer chromatography. The compounds described herein may be prepared in a variety of ways known to one skilled in the art.

The procedures described herein for synthesizing compounds the present disclosure may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts.

An Example of Synthetic Scheme for Compounds in Formula (I) and/or Formula (II)

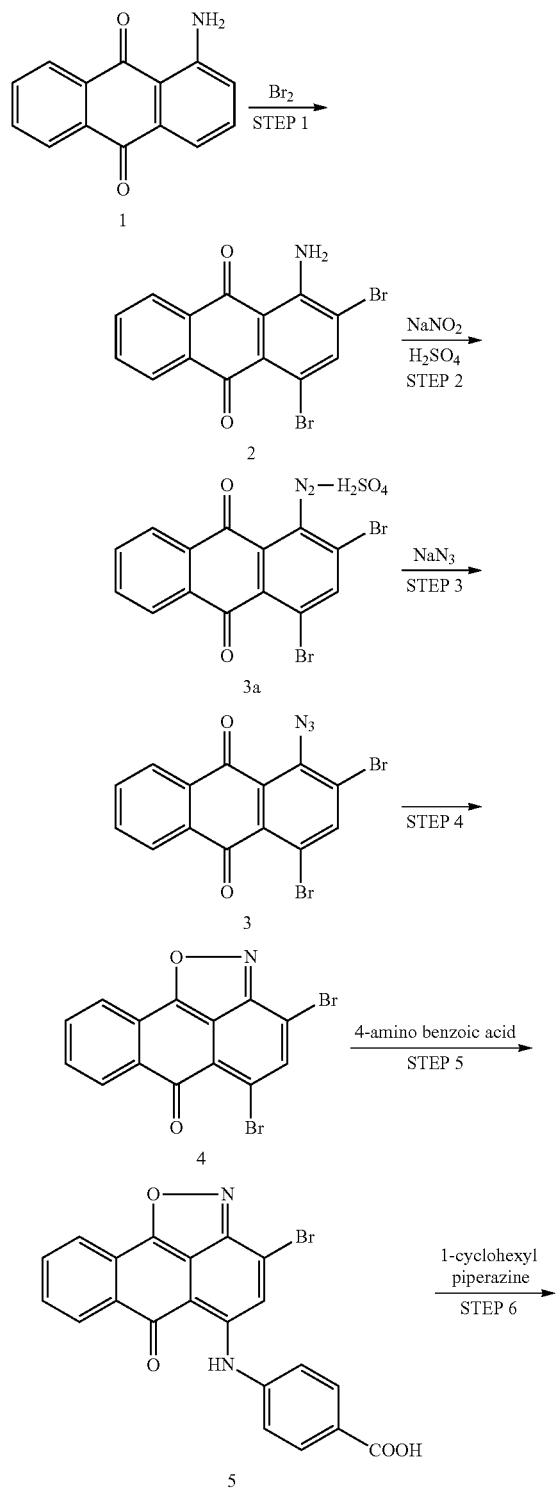

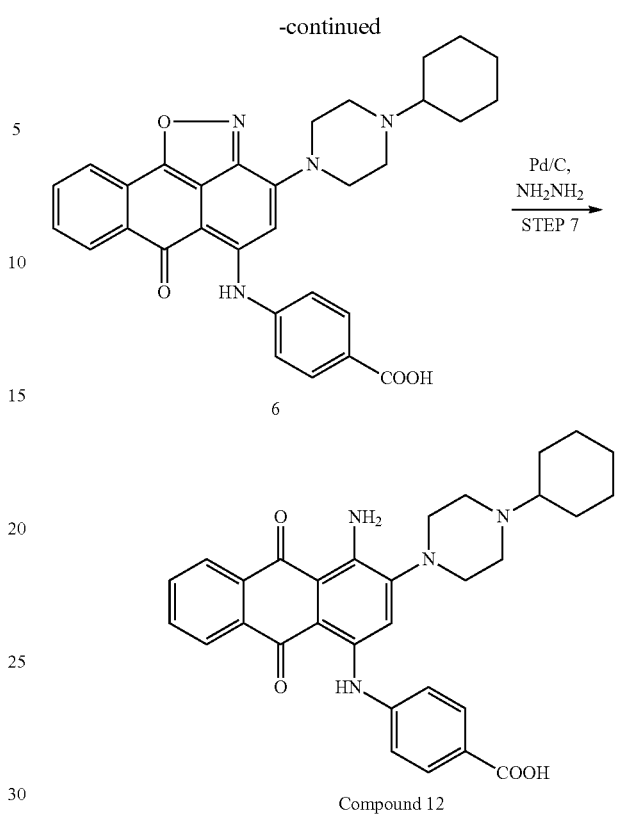

Preparation of Intermediate 2.

30.0 kg of 4-Amino-10-hydroxyanthracen-9(10H)-one (starting material 1) was suspended in MeOH (70 L). To the suspension, 53.7 kg of bromine was added to the suspension at 60° C. about 1 hr. After the addition of bromine, the reaction mixture was stirred at 50-60° C. for about 18-24 hours. The reaction mixture was then cooled. The resulting suspension was filtered, washed with MTBE. The red solid was dried to give Intermediate 2 as a red solid (~50.0 kg, yield 98%). HPLC analysis showed 96% purity. $^1$H-NMR (CDCl$_3$, 300 Hz) δ 8.26 (m, 2H), 8.09 (s, 1H), 7.80 (m, 2H).

Preparation of Intermediate 3a.

2.99 kg of NaNO$_2$ was added to cooled H$_2$SO$_4$ (27.8 L) solution gently. The mixture was stirred at 35° C. for 1 hr. Intermediate 2 (15.0 kg) was then added to the mixture and stirred at 50-55° C. for 4 h. After cooled to room temperature, the reaction mixture was poured into crushed ice. The yellow solid was precipitated out. The solid was collected by filtration, washed with ice-water, followed by 1:1 mixture of ethanol/MTBE to give a wet solid, which was dried. 24.7 kg of the crude damp product was obtained. The product was used for the next step without further purification.

Preparation of Intermediate 3.

A 100 L jacketed reactor was charged with the solution of NaN$_3$ (2.73 kg) in water. Intermediate 3a was added at room temperature, and the mixture was stirred at room temperature overnight. An aqueous solution of NaOH (6N) was then added slowly to the mixture. Then the solid was collected by filtration and washed with water. The filtrate cake was slurred with water, filtered, and washed with water, and followed by the mixture of acetone/water (9:1), air dried to give crude Intermediate 3 (23.2 kg of damp solid). HPLC analysis showed 95% purity. $^1$H-NMR (300 MHz, DMSO-d$_6$) δ 8.51 (s, 1H), 8.11-8.15 (m, 2H), 7.91-7.94 (m, 2H).

Preparation of Intermediate 4.

26.5 kg of crude Intermediate 3 was added to toluene at about 50-70° C. The mixture was then stirred at 50-70° C. overnight. After the reaction temperature was cooled to RT, the solid product was collected. The filter cake was washed with MeOH. The solid obtained was re-suspended in MeOH and stirred at room temperature for about 1-3 hour. After filtration, 13.3 kg of the wet product of Intermediate 4 was obtained as a yellow solid. HPLC analysis showed 98.7% purity. $^1$H-NMR (300 MHz, DMSO-d$_6$): δ 8.27 (m, 2H), 8.13 (m, 1H), 7.91 (m, 1H), 7.78 (m, 1H).

Preparation of Intermediate 5.

Mixing 4-amino benzoic acid and lithium hydroxide in DMAc, then adding 3,5-dibromo-6H-anthra[1,9-cd]isoxazol-6-one into the mixture at about 40-60° C. Stirring the reaction mixture for up to 24 hours. Adding MTBE to the reaction mixture. Filtering the solid and drying to get 4-((3-bromo-6-oxo-6H-anthra[1,9-cd]isoxazol-5-yl)amino)benzoic acid (Intermediate 5).

Preparation of Intermediate 6.

Dissolving Intermediate 5 in DMSO, then adding triethylamine and 1-cyclohexyl piperazine into the solution at temperature about 50-70° C. Adding MTBE and MeOH solution. Isolation and washing of the wet cake with MTBE and MeOH followed by filtering provided Intermediate 6 as a solid.

Preparation of Compound 12.

In a flask, Intermediate 6, Pd/C and hydrazine were mixed and heated for about 4 hours. Reaction mixture was cooled to room temperature and filtered, and then it was redissolved in TFA/DMAc and active charcoal, and then filtered through celite. NaHCO$_3$ was added to neutralize the mixture and the solid was collected by filtration. Compound 12 was purified and dried. It gave about 99% (HPLC, area %) purity. Mass spectra gave [M+1]=525.5. $^1$H-NMR (300 MHz, DMSO-d6), ppm (δ): 12.36 (1H, s), 8.27 (2H, d), 7.95 (2H, d), 7.85 (2H, t), 7.42 (2H, d), 7.25 (1H, s), 2.96 (4H, m), 2.74 (4H, m), 2.27 (2H, m), 1.57-1.80 (6H, m), 1.06-1.23 (5H, m).

5.3 Biological Activities

Compound Inhibition in a Radiometric Based Mixed Micelle Assay:

In a final reaction volume of 25 μL, TrkA (h) (3 nM) is incubated with the kinase reaction buffer (20 mM HEPES (pH 7.5), 10 mM MgCl2, 1 mM EGTA, 0.02% Brij 35, 0.02 mg/ml BSA, 0.1 mM Na3VO4, 2 mM DTT, 1% DMSO), 0.2 mg/ml substrate PolyEY(4:1) and 2 nM MnCl$_2$, and [$^{33}$P-ATP](specific activity approx. 500 cpm/pmol, concentration as required). The reaction is initiated by the addition of the MgATP mix. After incubation for at least 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting. TrkA: Recombinant Human Cytoplasmic Domain (amino acids 441-796), Histidine-tagged, expressed in insect cells. Activated in vitro via auto-phosphorylation. Mw=42.8 kDa. Substrates for kinases: poly(EY) for TRKA; poly(EY)(4:1) with 2 mM MnCl$_2$, average Mw=16 kDa Standard conditions (unless otherwise specified): 30 nM TRKA, 0.2 mg/ml poly(EY)+2 mM MnCl$_2$, and 10 μM ([γ-$^{33}$P]) ATP. Using the similar assay condition with other kinases of recombinant human cytoplasmic domain, the activities of other kinases could be also measured.

The TrkA kinase antagonist activity of a compound which may be used in the present disclosure may be determined by these assays. In particular, the compounds of the present disclosure aforementioned examples, including Table 1 had activity in antagonizing the TrkA kinase activity in the aforementioned assays, generally with an IC50 of less than about 25 μM. Preferred compounds within the present disclosure had activity in antagonizing the TrkA kinase activity in the aforementioned assays with an IC50 of less than about 2.5 μM. Further preferred compounds within the present disclosure had activity in antagonizing the TrkA kinase activity in the aforementioned assays with an IC50 of less than about 0.25 μM. The much further preferred compounds within the present disclosure had activity in antagonizing the TrkA kinase activity in the aforementioned assays with an IC50 of less than about 0.1 μM. For examples, Compound A of the present disclosure has an IC50 of 0.085 μM; Compound 12 of the present disclosure has about 99.6% inhibition of TrkA kinase at 10 μM concentration or an IC50 of about 50 to 150 nM and has more than about 10 μM of the IC50 values antagonizing, for instances, the following structurally related protein kinases and other more than 400 kinases, including TrkB, TrkC, ABL1, AKT1, ALK5/TGFB-R1, ARAF, AXL, BMX, BTK, CDK1/cyclinB, CDK2/cyclinA, CDK2/cyclinE, c-MET, c-Src, EPHA1, FES/FPS, FGFR1, FGR, FLT1, FLT3 (CD), FMS, FYN, IGF-1R, IR, ITK, JAK3, JNK3, LCK, LYN, MEK1, MEK2, MLK1/MAP3K9, MUSK, P38a/MAPK14, P38b/MAPK11, PDGFRa, PDGFRb, PKA, PKCalpha, PKCbetaI, PKCbetaII, PKCdelta, PKCepsilon, PKCeta, PKCgamma, PKCiota, PKCmu/PKD1, PKCtheta, PKCzeta, PKD2/PRKD2, PKG1a, PKG1b, RAF1, RET, TEC, TGFbR2, TIE2/TEK, VEGFR2/KDR, VEGFR3/FLT4 (duplicate, with a positive control compound of a pan-kinase inhibitor, staurosporine or K-252a). Such a result is indicative of the intrinsic activity of the compounds in use as isoform-selective antagonists of TrkA kinase activity.

Compound Inhibition in a Live, Whole Cell Based Functional Assay:

There are several methods to measure whole length TrkA activation stimulated by its natural ligand or agonist NGF in live cells. For example, the PathHunter Profiling services offered by DiscoveRx (Fremont, Calif.). The PathHunter technology is an adaptation of enzyme fragment complementation that provides a novel, generic functional cell-based assay format for detecting protein-protein interactions. In this cell-based assay approach, with U2OS cell background, a small peptide epitope (PK) is expressed recombinantly on the intracellular C-terminus of TrkA (human full length). This is co-expressed with a larger sequence, termed enzyme acceptor (EA) that is attached to a cytoplasmic protein SHC1 which will interact with TrkA intracellularly. NGF induced activation of TrkA receptor causes either homo- or hetero-dimerization of TrkA resulting in cross-phosphorylation. The SHC1-EA fusion protein then binds the phosphorylated TrkA receptor forcing complementation of the PK and EA fragment. This interaction generates an active beta-galactosidase enzyme, which is detected using a chemiluminescent substrate.

In such cell-based functional assays, for example, Compound 12 of the present disclosure inhibits NGF stimulated TrkA activation at low nanomolar concentration (cellular IC$_{50}$ is about 50-150 nM), while virtually has no effect on either BDNF stimulated TrkB, or NT3 stimulated TrkC activation (IC$_{50}$>10 μM in both cases, triplicate, with a positive control compound of pan-kinase inhibitor, staurosporine or K-252a, an internal agonist control and a negative control compound).

Mode of Inhibition with Respect to ATP.

The TrkA kinase assays were performed at room temperature. Four concentrations of compounds (0, 0.037, 0.11, and 0.33 µM) were added into Enzyme/substrate mixture using acoustic technology, and incubated for 40 min to ensure all compounds were equilibrated and bound to the enzyme. Then various concentrations of ATP (10, 100, 200, 350, and 500 µM ATP with 0.2 mg/ml poly(EY)) were added to initiate the reaction. The activity was monitored every 5-15 min for time course. Such kinetic analysis shows that Compound D, for example, inhibits TrkA non-competitively with respect to ATP: Lineweaver-Burk double-reciprocal plots showing differences in Vmax but not in km for the 4 conditions.

Mode of Inhibition with Respect to Substrate.

The kinase assays were performed similar manner to ATP study. Various concentrations of compounds (0, 0.037, 0.11, and 0.33 µM) were added into Enzyme/substrate mixture using acoustic technology, and incubated for 40 min to ensure all compounds were equilibrated and bound to the enzyme. Then 10 µM ATP and various concentrations of substrate (0.02, 0.05, 0.1, 0.2, and 0.5 mg/ml poly(EY)) were added to initiate the reaction. The activity was monitored every 5-15 min for time course. Such kinetic analysis shows that Compound D, for example, inhibits TrkA non-competitively with respect to substrate: Lineweaver-Burk double-reciprocal plots showing differences in Vmax but not in km for the 4 conditions.

Cell Viability and Proliferation Assays.

To assess the chemosensitivity of tumor cells, cell viability is measured by CellTiter-Glo® Luminescent Cell Viability Assay (Promega; WI, USA) per the manufacturer's instruction. Briefly, $5 \times 10^3$ to $7 \times 10^5$ cells/ml are cultured in sterile 96-well plates in the presence of increasing concentrations of the drugs (test article, 0 to 100 µM), or vehicle in RPMI medium. The plates are then incubated for 24 to 96 h, and then 100 µl of CellTiter-Glo reagent is added to lyse the cells. After a 10-min incubation at room temperature, the luminescence is recorded in a luminometer with an integration time of 1 s per well. The luminescence signals for the drug-treated cells are normalized by the luminescence signal obtained from vehicle-treated cells. As an alternative method to quantitate cell viability, the trypan blue exclusion dye method was used. Vehicle- or drug-treated cells were assayed by adding trypan blue solution (0.4% in phosphate-buffered saline [PBS]) to the culture medium. After 3 min, the number of dead cells that retained the dye is compared to the total number of cells to calculate cell viability. GraphPad Prism 5 software is used to calculate IC50 and plot effect-dose curve of drugs. Multiplate reader: EnVision 2104 (PerkinElmer). % of control variability=100*[(X(drug_treated)−L(baseline))/(H(vehicle_control)−L(baseline))]. Such assays show that for example, Compound 12, has IC50 values about 2 to 5 µM in human pancreatic cancer cells (from ATCC) of AsPC-1, MIA PaCa-2, BxPC-3, Capan-1 and Panc-1; about 5 µM in human liver cancer cells of SK-HEP-1 and HepG2; and about 7 µM in human stomach cancer cells of NCI-N87, after 24 incubation. Taxol, erlotinib, sorafenib and gemcitabine are used as controls, and the compounds of present disclosures are synergistic or additive with gemcitabine in pancreatic cancer cells or are synergistic or additive with sorafenib in liver cancer cells.

Pharmacokinetic and Bioavailabilities after Oral and Intraperitoneal (i.p.) Treatment Bioavailability in CD-1 Mice.

Pharmacokinetics and bioavailability of after oral and i.p. treatment in CD-1 mice (n=4 per dose group) are determined. For example, for Compound 12, the oral bioavailability in CD-1 mice is about 100% after 50 mg/kg oral dosing of the drug; i.p. bioavailability is about 100% after 50 mg/kg i.p. dosing of the drug; the elimination half-life is about 1 h after intravenous dosing and about 3.5 h after i.p. dosing and about 4.5 h after oral dosing, of the Compound 12.

Chronic Constriction Injury (CCI) Model of Neuropathic Pain in Rats.

The CCI model is one of the most commonly used mono-neuropathic pain model firstly described in details by Bennett and Xie (Bennett G J, Xie Y K. Pain. 1988; 33(1):87-107). It mimics important clinical chronic pain symptoms such as mechanical allodynia and thermal hyperalgesia. Chronic constriction injury of the sciatic nerve was produced by tying four loose ligatures around the left sciatic nerve according to the method of Bennett and Xie. This procedure resulted in tactile allodynia in the left hindpaw. Calibrated von Frey filaments were used to determine the lowest mechanical (tactile) threshold required to evoke a brisk paw withdrawal reflex in the rat hindpaws. Rats were allowed to acclimatize in wire mesh cages for 15-20 min prior to von Frey testing. Assessment of paw withdrawal thresholds (PWTs) using von Frey filaments was undertaken prior to CCI-surgery (pre-surgery baseline on day 0). Before the drug dosing on day 14, the pre-dose baseline was recorded for each rat. Rats were included in the study only if they did not exhibit motor dysfunction (e.g., paw dragging or dropping) and their PWT was below to 4 g. Drug-naïve CCI-rats (n=4-6 per group) were used. The oral vehicle was 0.5% CMC-Na/0.1% Tween 80 in distilled water. The positive control gabapentin was dissolved in the vehicle and orally given at 100 mg/kg (by oral gavage). Test compound was suspended in the vehicle and orally given at 50 mg/kg and 100 mg/kg. Each CCI-rat was administered a single oral dose of test compound, gabapentin or vehicle control, 2 hours before assessment of PWT. In such rat neuropathic pain model that, for example, Compound 12, has shown about 48% relative analgesic effect at 150 mg/kg oral dose compared to analgesic effect produced by morphine (HCl) at 3 mg/kg, s.c.

The results have demonstrated that oral administration of, for example, Compound D of present disclosure significantly reduced mechanical allodynia in CCI rats of neuropathic pain model in a dose-dependent manner. In addition, at the same oral dose of 100 mg/kg, Compound D is about 98% more effective in suppressing mechanical allodynia in CCI neuropathic pain compared to gabapentin, the current gold standard medication for neuropathic pain, while even 50 mg/kg oral Compound D is about 28% more effective than 100 mg/kg oral gabapentin. Of note, CCI-rats dosed with gabapentin have shown drowsiness or motor incoordination, which is consistent with known side effect of gabapentin. However, no such effect or other abnormality was observed in CCI-rats dosed with Compound D.

Furthermore, there is no statistically significant difference of anti-allodynia effects as measured on day 14 and on day 20 for the same group of CCI-rats treated with the same single oral dose of Compound D at 100 mg/kg, indicating that there is no tolerance issue.

Spinal Nerve Ligation (SNL) Mono-Neuropathic Pain Model in Rats.

The surgical procedure will be performed according to the method firstly described by Kim and Chung (Kim S H, Chung J M. Pain. 1992; 50(3):355-63). This procedure will result in tactile allodynia in the left hindpaw. Rats will be included in the study only if they do not exhibit motor dysfunction (e.g., paw dragging or dropping) and their PWT is below to 4.0 g. The Dose-Response Anti-Allodynia Effects of Test Compound:

On day 14 after surgery, rats will be treated with test compound at one of four doses, vehicle or positive control by oral gavage, and PWT is determined by calibrated von Frey filaments at time points of 0 (right before the drug dosing, Pre-Dose Baseline), 0.5, 1, 2, 4 and 6 hr.

Tolerance Effects:

6 days following the day 14 test, i.e. on day 20 after surgery, the same procedure on day 14 will be repeated on day 20 with the same group of CCI-rats treated with the same (effective) dose as on day 14. The results of anti-allodynia effects of test compound as tested on day 14 and on day 20 will be compared to see if there is any tolerance effect of test compound in animals.

The Anti-Allodynia Effects of Repeated Administration of Test Compound:

Administration of test compound will start on day 7 after surgery, once a day for 7 days. PWT will be determined by calibrated von Frey filaments once a day, 2 hour after compound dosing. After 7 days dosing, the measurement will be continued, every other day without compound dosing for another 7 days. PWT will be determined at the time points as given above.

Thermal Hyperalesia Effects.

Thermal hyperalgesia may be assessed in the SNL rats by plantar test with a single dose of TEST COMPOUND at the time points given above.

Streptozotocin-Induced Diabetic Poly-Neuropathic Pain Model.

Diabetic peripheral neuropathy is a long-term complication of diabetes mellitus. Rats will receive i.p. injections of streptozotocin (STZ, 50 mg/kg dissolved in citrate buffer at pH 4.5 immediately before the injection) to induce insulin-dependent diabetes mellitus and produce tactile allodynia. One week later, blood glucose level will be assayed, from samples taken from the tail vein, using standard test strips and colorimeter. Only animals with a blood glucose level >350 mg/dL will be considered diabetic and included for the testing. Typical features of neuropathic pain (tactile allodynia) will be developed in hindpaws beginning around 2 to 3 weeks after STZ injection. After 4 weeks, a stable level of allodynia will be usually reached. At this point, the rats with PWT below 4.5 g will be enrolled for compound testing. The allodynic state will remain intact until the $8^{th}$ week after STZ injection. All animals will be observed daily and weighed regularly during the study period. This model of neuropathic pain mimics the symptoms of neuropathy in diabetic patients (Lynch J J, 3rd, et al Eur J Pharmacol. 1999; 364(2-3):141-6; Calcutt N A, J Neurol Sci. 2004; 220(1-2):137-9).

The Dose-Response Anti-Allodynia Effects of Test Compound:

On day 28 after STZ injection, rats will be treated with test compound at one of four doses, or controls (vehicle and positive) by oral gavage, and PWT will be determined by calibrated von Frey filaments at time points of 0 (right before the drug dosing, Pre-Dose Baseline), 0.5, 1, 2, 4 and 6 hr.

Tolerance Effects:

6 days following the day 28 test, i.e. on day 34 after STZ injection, the same procedure on day 28 will be repeated on day 34 with the same group of STZ-rats treated with the same (effective) dose as on day 28. The two results of anti-allodynia effects of test compound as measured on day 28 and on day 34 will be compared to see if there is any tolerance effect of test compound in animals.

The Anti-Allodynia Effects of Repeated Administration of Test Compound:

Administration (p.o.) of test compound will start on day 21 after STZ injection, once a day for 7 days. PWT will be determined by calibrated von Frey filaments once a day, 1 hour after compound dosing. After 7 days dosing, the measurement will be continued, every other day without compound dosing for another 7 days. PWT is determined at the time points as given above. The thermal hyperalgesia assessment by plantar test may be performed in STZ models with a single dose and PWL will be determined, at time points as given above.

Carrageenan Pain Model

The carrageenan model is a fast, reliable model used to assess the ability of analgesics to block inflammatory pain. The analgesic effects of test article combinations on pain generation are assayed using the carrageenan-induced pain model in rats. Adult male Sprague-Dawley rats are administered study drugs orally (vehicle, compounds of present disclosure) once daily for 2 days (day −2 and day −1) and 30 minutes prior to the carrageenan injection on day 0 (time=0). For the carrageenan injection, animals are lightly anesthetized and 0.1 ml of 2% carrageenan is injected into the plantar surface of the right hind paw. The positive control indomethacin (30 mg/kg, p.o.) is administered orally immediately before the carrageenan injection. Paw volumes (right and left) are measured using a Plethysmometer before drug administration on day −2 and serve as a baseline measurement. The paw volumes are measured again two hours post carrageenan injection. The degree of mechanical allodynia is measured by a blinded observer using Von Frey filaments applied to the plantar surface of the hind paws in an increasing numerical order. Each filament increases the force applied on the paw. The filaments are applied until animal paw withdrawal is achieved. This procedure is carried out before drug administration (day −2), on day −1 and on day 0 at time=0, 20, 40, 60, 80 and 120 minutes post-carrageenan. The force (expressed in grams) required for paw withdrawal after carrageenan injection is subtracted from the force required for paw withdrawal before carrageenan injection. Results are expressed as mean change from baseline across five timepoints post carrageenan injection. In such rat pain model that, for example, Compound 12, has shown about 85% relative analgesic effect at 150 mg/kg oral dose compared to analgesic effect, about 100% produced by indomethacin (30 mg/kg, p.o.).

In Vivo Evaluation of Anti-Tumor Efficacy of a Compound of Formula (I) and/or Formula (II) in PANC-1 Subcutaneous Human Pancreatic Cancer Xenograft Mouse Model.

In vivo therapeutic efficacy of a Compound of Formula (I) and/or Formula (II) (test article) and its combination with gemcitabine in PANC-1 subcutaneous human pancreatic cancer xenografts in BALB/c female nude mice (with body weight ranged 18-23 grams) was performed.

Animal Housing:

Animals were kept in laminar flow rooms at constant temperature and humidity with 4 or 3 animals in each cage. Temperature: 22±3° C. Humidity: 50±20%. Light cycle: 12 hours light and 12 hours dark. Cages: Polycarbonate cages of 300 mm×180 mm×150 mm embedded with the soft wood material were used. The bedding was changed twice a week. Diet: Animals had free access to a certified commercial laboratory diet. Concentrations of contaminants in the diet are routinely analyzed by the manufacturers to ensure the contaminants are below their allowable maximum and thus would not affect the tumor growth.

Water:

Animals had free access to sterile drinking water. Cage identification: The identification labels for each cage contained the following information: number of animals, sex, strain, date received, treatment, group number and the starting date of the treatment. Briefly, PANC-1 cell line was originally purchased from the ATCC (CRL-1469) and the PANC-1 primary cell line was derived from the PANC-1 subcutaneously xenograft tumors. The PANC-1 primary cells were maintained in vitro as monolayer culture in DMEM medium supplemented with 10% heat inactivated fetal bovine serum, 100 U/ml penicillin and 100 μg/ml streptomycin and L-glutamine (2 mM) at 37° C. in an atmosphere of 5% $CO_2$ air. The cells growing in exponential phase were harvested and counted for tumor inoculation.

Tumor Cell Inoculation and Randomization:

Each animal was inoculated subcutaneously on the right flank with the PANC-1 primary tumor cells ($5 \times 10^6$/animal) in 0.1 mL of PBS. Tumor development was allowed undisrupted until mean tumor volume reached approximately 85 $mm^3$. Animals were then randomized into 6 groups, with each group consisting of 8 animals. The test articles were administered to the tumor-bearing animals according to predetermined regimens. All the procedures related to animal handling, care and the treatment in this study were performed according to guidelines approved by the Institutional Animal Care and Use Committee (IACUC) of the testing lab following the guidance of the Association for Assessment and Accreditation of Laboratory Animal Care (AAALAC). At the time of routine monitoring, the animals were checked for any effects of tumor growth on normal behavior such as mobility, food and water consumption (by looking only), body weight (BW) gain/loss (BW was measured twice weekly), eye/hair matting and any other abnormal effect. Death and observed clinical signs were recorded on the basis of the numbers of animals within each subset.

Tumor Measurement and the Endpoints:

The major endpoint was to evaluate if the tumor growth could be inhibited. Tumor measurement was conducted twice weekly with a caliper and the tumor volume (mm3) is estimated using the formula: $TV = a \times b^2 / 2$, where a and b are long and short diameters of a tumor, respectively. The tumor sizes were then used for T/C value and TGI (tumor growth inhibition), which are indicators of anti-tumor effectiveness. The T/C value (in percent) is an indication of antitumor effect. T and C are the mean volumes of the treated and control groups, respectively, on a given day. BW change, expressed as %, is calculated using the following formula: BW change (%)= (BW_DayX/BW_Day0)×100, where BW_DayX is BW on a given day, and BW_Day0 was BW on Day 0 (tumor inoculation).

Tumor Sample Collection:

Two tumor samples from Group 1, 2 and 3, respectively; six tumor samples from Group 4; five tumor samples from Group 5 and 6, respectively, were snap frozen in liquid nitrogen and kept at −80° C. Total 22 tumor samples were collected.

Statistical Analyses:

A one-way ANOVA was performed to compare tumor volumes among groups. All data were analyzed using the SPSS 17.0 software; p<0.05 was considered statistically significant. The in vivo anti-tumor efficacy of Compound 12, either alone or in combination with gemcitabine are listed in following two tables.

The results indicated that the Compound 12 was efficacious in reducing tumor growth, either alone or in combination with the current standard care medicine, gemcitabine and, the combination of Compound 12 and gemcitabine showed great synergistic efforts and, having greater tumor reduction than either Compound 12 or gemcitabine alone.

Mean Tumor Volumes of Different Groups

| | Tumor volume $(mm^3)^a$ | | | | | |
|---|---|---|---|---|---|---|
| Days | Vehicle | Gemcitabine 10 mg/kg | Gemcitabine 20 mg/kg | Compound-12 | Gemcitabine 10 mg/kg + Compound-12 | Gemcitabine 20 mg/kg + Compound-12 |
| 7  | 84 ± 5   | 83 ± 4   | 83 ± 3   | 84 ± 4   | 85 ± 5   | 82 ± 4  |
| 11 | 149 ± 11 | 142 ± 12 | 109 ± 8  | 111 ± 5  | 90 ± 6   | 89 ± 6  |
| 14 | 193 ± 15 | 174 ± 9  | 138 ± 9  | 157 ± 15 | 128 ± 12 | 115 ± 7 |
| 18 | 357 ± 25 | 346 ± 21 | 184 ± 13 | 234 ± 8  | 138 ± 8  | 127 ± 10 |
| 19 | 402 ± 27 | 374 ± 19 | 216 ± 18 | 276 ± 27 | 150 ± 10 | 143 ± 7 |

Note:
$^a$Mean ± SEM

Antitumor Activity of Compound-12 and its Combination with Gemcitabine in Treatment of Subcutaneous PANC-1 Human Pancreatic Cancer Xenograft Model

| Treatment | Tumor Volume $(mm^3, D18)^a$ | P value$^b$ | TGI (%, D18) |
|---|---|---|---|
| G1: Vehicle | 357 ± 25 | — | — |
| G2: Gemcitabine 10 mg/kg | 346 ± 21 | 1.000 | 3 |
| G3: Gemcitabine 20 mg/kg | 184 ± 13 | 0.001 | 48 |
| G4: Compound-12 | 234 ± 8 | 0.018 | 34 |
| G5: Gemcitabine 10 mg/kg + Compound-12 | 138 ± 8 | <0.001 | 61 |
| G6: Gemcitabine 20 mg/kg + Compound-12 | 127 ± 10 | <0.001 | 64 |

Note:
$^a$Mean ± SEM; $^b$ vs. control.
P values: G2 vs. G3 < 0.001; G2 vs. G4 = 0.008; G2 vs. G5 < 0.001; G2 vs. G6 < 0.004; G3 vs. G4 = 0.094; G3 vs. G5 = 0.134; G3 vs. G6 = 0.062; G4 vs. G5 < 0.001; G4 vs. G6 < 0.001; G5 vs. G6 = 0.998

5.4 Therapeutic Uses

In accordance with the present disclosure, a compound of the present disclosure, or a salt, solvate, ester, and/or a prodrug thereof, or a pharmaceutical composition containing the compound, or a salt, solvate, ester, and/or a prodrug thereof, is administered to a patient, preferably a human, suffering from a variety of disorders. These include cancers, anxiety, generalized pain disorder, acute pain, chronic pain, inflammatory pain and neuropathic pain.

While the disclosure has been described and illustrated with reference to certain preferred embodiments, those skilled in the art will appreciate that various changes, modifications and substitutions can be made therein without departing from the spirit and scope of the disclosure.

5.5 Therapeutic/Prophylactic Administration

The present compounds, or salts, solvates, esters, and/or prodrugs thereof, or pharmaceutical compositions containing the present compounds, or salts, solvates, esters, and/or prodrugs thereof, may be advantageously used in human medicine. As previously described in Section 6.4 above, the present compounds are useful for the treatment or prevention of various diseases.

When used to treat or prevent the above-mentioned diseases or disorders, the present compounds may be administered or applied solely, or in combination with other active agents (e.g., other pain agents).

The present disclosure provides methods of treatment and prophylaxis by administration to a patient in need of such treatment a therapeutically effective amount of one or more compounds of the present disclosure, or salts, solvates, esters, and/or prodrugs thereof. The patient may be an animal, more preferably, a mammal and most preferably, a human.

The present compounds, or salts, solvates, esters, and/or prodrugs thereof, may be administered orally. The present compounds, or salts, solvates, esters, and/or prodrugs thereof, may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner and will depend in-part upon the site of the medical condition. In most instances, administration will result in the release of the present compounds, or salts, solvates, esters, and/or prodrugs thereof, into the bloodstream of a patient.

In specific embodiments, it may be desirable to administer one or more of the present compounds, or salts, solvates, esters, and/or prodrugs thereof, locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In some embodiments, administration can be accomplished by direct injection at the site (or former site) of cancer or arthritis.

In certain embodiments, it may be desirable to introduce one or more the present compounds, or salts, solvates, esters, and/or prodrugs thereof, into the central nervous system of a patient by any suitable route, including intraventricular, intrathecal and epidural injection. Intraventricular injection may be facilitated by an intraventricular catheter, for example, attached to a reservoir, such as an Ommaya reservoir.

The present compounds, or salts, solvates, esters, and/or prodrugs thereof, may also be administered directly to the lung by inhalation. For administration by inhalation, the present compounds, or salts, solvates, esters, and/or prodrugs thereof, may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas), may be used to deliver compounds of the disclosure directly to the lung.

Alternatively, a Dry Powder Inhaler ("DPI") device may be used to administer the present compounds, or salts, solvates, esters, and/or prodrugs thereof, to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. For example, capsules and cartridges of gelatin for use in an inhaler or insufflator may be formulated containing a powder mix of a compound of the disclosure and a suitable powder base such as lactose or starch for these systems.

Another type of device that may be used to deliver the present compounds, or salts, solvates, esters, and/or prodrugs thereof, to the lung is a liquid spray device supplied, for example, by Aradigm Corporation, Hayward, Calif. Liquid spray systems use extremely small nozzle holes to aerosolize liquid drug formulations that may then be directly inhaled into the lung.

In some embodiments, a nebulizer is used to deliver the present compounds, or salts, solvates, esters, and/or prodrugs thereof, to the lung. Nebulizers create aerosols from liquid drug formulations by using, for example, ultrasonic energy to form fine particles that may be readily inhaled (see e.g., Verschoyle et al., *British J. Cancer,* 1999, 80, Suppl. 2, 96. Nebulizers are available from a number of commercial sources such as Sheffield/Systemic Pulmonary Delivery Ltd. Aventis and Batelle Pulmonary Therapeutics.

In other embodiments, an electrohydrodynamic ("EHD") aerosol device is used to deliver the present compounds, or salts, solvates, esters, and/or prodrugs thereof, to the lung. EHD aerosol devices use electrical energy to aerosolize liquid drug solutions or suspensions (see e.g., Noakes et al., U.S. Pat. No. 4,765,539). The electrochemical properties of the formulation may be important parameters to optimize when delivering the present compounds, or salts, solvates, esters, and/or prodrugs thereof, to the lung with an EHD aerosol device and such optimization is routinely performed by one of skill in the art. EHD aerosol devices may more efficiently deliver drugs to the lung than existing pulmonary delivery technologies.

In other embodiments, the present compounds, or salts, solvates, esters, and/or prodrugs thereof, can be delivered in a vesicle, in particular a liposome (See, Langer, 1990, *Science,* 249:1527-1533; Treat et al., in "Liposomes in the Therapy of Infectious Disease and Cancer," Lopez-Berestein and Fidler (eds.), Liss, New York, pp. 353-365 (1989); see generally "Liposomes in the Therapy of Infectious Disease and Cancer," Lopez-Berestein and Fidler (eds.), Liss, New York, pp. 353-365 (1989)).

In other embodiments, the present compounds, or salts, solvates, esters, and/or prodrugs thereof, can be delivered via sustained release systems. In still other embodiments, the sustained release system is an oral sustained release systems. In still other embodiments, a pump may be used (See, Langer, supra; Sefton, 1987, *CRC Crit Ref Biomed Eng.* 14:201; Saudek et al., 1989, *N. Engl. J Med.* 321:574).

In still other embodiments, polymeric materials can be used in the pharmaceutical compositions containing the present compounds, or salts, solvates, esters, and/or prodrugs thereof. (for exemplary polymeric materials, see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, *J Macromol. Sci. Rev. Macromol Chem.* 23:61; see also Levy et al., 1985, *Science* 228: 190; During et al., 1989, *Ann. Neurol.* 25:351; Howard et al., 1989, *J. Neurosurg.* 71:105). In still other embodiments, polymeric materials are used for sustained release delivery of oral pharmaceutical compositions. Exemplary polymers include, but are not limited to, sodium carboxymethylcellulose, hydroxypropylcellulose, hydroxypropylmethylcellulose and hydroxyethylcellulose (most preferred, hydroxypropyl methylcellulose). Other cellulose ethers have been described (Alderman, *Int. J. Pharm. Tech. & Prod. Mfr.*, 1984, 5(3) 1-9). Factors affecting drug release are well known to the skilled artisan and have been described in the art (Bamba et al., *Int. J. Pharm.*, 1979, 2, 307).

In other embodiments, enteric-coated preparations can be used for oral sustained release administration. Coating materials include, but are not limited to, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still other embodiments, osmotic delivery systems are used for oral sustained release administration (Verma et al., *Drug Dev. Ind. Pharm.*, 2000, 26:695-708). In still other embodiments, OROS™ osmotic devices are used for oral sustained release delivery devices (Theeuwes et al., U.S. Pat. No. 3,845,770; Theeuwes et al., U.S. Pat. No. 3,916,899).

In still other embodiments, a controlled-release system can be placed in proximity of the target of the present compounds, or salts, solvates, esters, and/or prodrugs thereof, thus requiring only a fraction of the systemic dose (See, e.g., Goodson, in "Medical Applications of Controlled Release," supra, vol. 2, pp. 115-138 (1984)). Other controlled-release systems discussed in Langer, 1990, *Science* 249:1527-1533 may also be used.

5.6 Pharmaceutical Compositions of the Disclosure

In one aspect, the present disclosure provides pharmaceutical compositions comprising one or more compounds of the present disclosure including the compound having structural formula (I) and/or formula (II) and any of their subgeneric groups and specific embodiments described above in Section 5.2.

The present pharmaceutical compositions contain a therapeutically effective amount of one or more compounds of the present disclosure, or salts, solvates, esters, and/or prodrugs thereof, preferably in purified form, together with a suitable amount of a pharmaceutically acceptable vehicle, so as to provide a form for proper administration to a patient. When administered to a patient, the present compounds and the pharmaceutically acceptable vehicles are preferably sterile. Water is a preferred vehicle when a compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the disclosure into preparations that can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy, Philadelphia College of Pharmacy and Science, 20$^{th}$ Edition, 2000).

For topical administration a compound may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent such as another anti-cancer agent.

In some embodiments, the present compounds, or salts, solvates, esters, and/or prodrugs thereof, are formulated in accordance with routine procedures as a pharmaceutical composition adapted for intravenous administration to human beings. Typically, compounds for intravenous administration are solutions in sterile isotonic aqueous buffer. For injection, the present compounds, or salts, solvates, esters, and/or prodrugs thereof, may be formulated in aqueous solutions, preferably, in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent. Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the present compounds, or salts, solvates, esters, and/or prodrugs thereof, are administered by infusion, it can be dispensed, for example, with an infusion bottle containing sterile pharmaceutical grade water or saline. When the present compounds, or salts, solvates, esters, and/or prodrugs thereof, are administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin; flavoring agents such as peppermint, oil of wintergreen, or cherry coloring agents and preserving agents, to provide a pharmaceutically palatable preparation. Moreover, in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the disclosure. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the disclosure with a pharmaceutically acceptable vehicle. In some embodiments, the pharmaceutically acceptable vehicle is a liquid such as alcohol, water, polyethylene glycol or a perfluorocarbon. Optionally, another material may be added to alter the aerosol properties of the solution or suspension of compounds disclosed herein. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

The present compounds, or salts, solvates, esters, and/or prodrugs thereof, may also be formulated in rectal or vaginal pharmaceutical compositions such as suppositories or retention enemas, e.g., containing conventional suppository bases such as cocoa butter or other glycerides.

In addition to the formulations described previously, the present compounds, or salts, solvates, esters, and/or prodrugs thereof, may also be formulated as a depot preparation. Such long acting formulations may be administered by implantation (for example, subcutaneously or intramuscularly) or by intramuscular injection. Thus, for example, the present compounds, or salts, solvates, esters, and/or prodrugs thereof, may be formulated with suitable polymeric or hydrophobic materials (for example, as an emulsion in an acceptable oil) or ion exchange resins, or as sparingly soluble derivatives, for example, as a sparingly soluble salt.

5.7 Therapeutic Doses

The present compounds, or a salt, prodrug or softdrug, salt of prodrug or softdrug, solvate or hydrate thereof and a pharmaceutically acceptable vehicle is provided, will generally be used in an amount effective to achieve the intended purpose. For use to treat or prevent diseases or disorders characterized by down regulated apoptosis the compounds and/or pharmaceutical compositions thereof, are administered or applied in a therapeutically effective amount.

The amount of the present compounds, or salts, solvates, esters, and/or prodrugs thereof, that will be effective in the treatment of a particular disorder or condition disclosed herein will depend on the nature of the disorder or condition, and can be determined by standard clinical techniques known in the art. In addition, in vitro or in vivo assays may optionally be employed to help identify optimal dosage ranges. The amount of the present compounds, or salts, solvates, esters, and/or prodrugs thereof, administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In some embodiment, the present compounds, or salts, solvates, esters, and/or prodrugs thereof, are delivered by oral sustained release administration. Dosing may be repeated intermittently, may be provided alone or in combination with other drugs and may continue as long as required for effective treatment of the disease state or disorder.

Suitable dosage ranges for oral administration (the oral unit dosage form) to a patient in need depend on the potency of the present compounds, but are generally between about 0.001 mg to about 200 mg of a compound of the disclosure per kilogram body weight; more preferably, between about 0.01 mg to about 50 mg of a compound of the disclosure per kilogram body weight; still more preferably, between about 0.05 mg to about 20 mg of a compound of the disclosure per kilogram body weight; and the patient is an animal; more preferably, a mammal; and most preferably, a human. Dosage ranges may be readily determined by methods known to the artisan of ordinary skill.

Suitable dosage ranges for intravenous (i.v.) administration to a patient in need are about 0.001 mg to about 100 mg per kilogram body weight; more preferably, between about 0.01 mg to about 20 mg of a compound of the disclosure per kilogram body weight; and the patient is an animal; more preferably, a mammal; and most preferably, a human. Suitable dosage ranges for intranasal administration to a patient in need are generally about 0.001 mg/kg body weight to about 10 mg/kg body weight; more preferably, between about 0.01 mg to about 1 mg of a compound of the disclosure per kilogram body weight; and the patient is an animal; more preferably, a mammal; and most preferably, a human. Suppositories generally contain about 0.01 milligram to about 50 milligrams of a compound of the disclosure per kilogram body weight and comprise active ingredient in the range of about 0.5% to about 10% by weight. Recommended dosages for intradermal, intramuscular, intraperitoneal, subcutaneous, epidural, sublingual or intracerebral administration to a patient in need are in the range of about 0.001 mg to about 200 mg per kilogram of body weight; and the patient is an animal; more preferably, a mammal; and most preferably, a human. Effective doses may be extrapolated from dose-response curves derived from in vitro or animal model test systems. Such animal models and systems are well-known in the art.

The present compounds, or salts, solvates, esters, and/or prodrugs thereof, are preferably assayed in vitro and in vivo, for the desired therapeutic or prophylactic activity, prior to use in humans. For example, in vitro assays can be used to determine whether administration of a specific compound of the disclosure or a combination of compounds is preferred for inducing apoptosis or signal transduction in cells which overexpress bcl-2 proteins or protein kinases. The present compounds, or salts, solvates, esters, and/or prodrugs thereof, may also be demonstrated to be effective and safe using animal model systems.

Preferably, a therapeutically effective dose of the present compounds, or salts, solvates, esters, and/or prodrugs thereof, will provide therapeutic benefit without causing substantial toxicity. Toxicity of the present compounds, or salts, solvates, esters, and/or prodrugs thereof, may be determined using standard pharmaceutical procedures and may be readily ascertained by the skilled artisan. The dose ratio between toxic and therapeutic effect is the therapeutic index. The present compounds, or salts, solvates, esters, and/or prodrugs thereof, generally exhibit particularly high therapeutic indices in treating apoptosis associated disease and disorders. The dosage of the present compounds, or salts, solvates, esters, and/or prodrugs thereof, will preferably be within a range of circulating concentrations that include an effective dose with little or no toxicity.

5.8 Combination Therapy

In certain embodiments of the present disclosure, the present compounds, or salts, solvates, esters, and/or prodrugs thereof, can be used in combination therapy with at least one additional active or therapeutic agent. The present compounds, or salts, solvates, esters, and/or prodrugs thereof, and the at least one additional active or therapeutic agent can act additively or, more preferably, synergistically. In some embodiments, the present compounds, or salts, solvates, esters, and/or prodrugs thereof are administered concurrently, sequentially, or separately with the administration of another therapeutic agent. Exemplary active or chemotherapeutic agents include, but are not limited to, aceglatone, aclarubicin, altretamine, aminoglutethimide; 5-aminogleavulinic acid, amsacrine, anastrozole, ancitabine hydrochloride, 17-1a antibody, antilymphocyte immunoglobulins, antineoplaston a10, asparaginase, pegaspargase, azacitidine, azathioprine, batimastat, benzoporphyrin derivative, bicalutamide, bisantrene hydrochloride, bleomycin sulphate, brequinar sodium, broxuridine, busulphan, campath-ih, caracemide, carbetimer, carboplatin, carboquone, carmofur, carmustine, chlorambucil, chlorozotocin, chromomycin, cisplatin, cladribine, *corynebacterium parvum*, cyclophosphamide, cyclosporin, cytarabine, dacarbazine, dactinomycin, daunorubicin hydrochloride, decitabine, diaziquone, dichlorodiethylsulphide, didemnin b., docetaxel, doxifluridine, doxorubicin hychloride, droloxifene, echinomycin, edatrexate, elliptinium, elmustine, enloplatin, enocitabine, epirubicin hydrochloride, erlotinib, estramustine sodium phosphate, etanidazole, ethoglucid, etoposide, fadrozole hydrochloride, fazarabine, fenretinide, floxuridine, fludarabine phosphate, fluorouracil, flutamide, formestane, fotemustine, gallium nitrate, gemcitabine, gusperimus, homoharringtonine, hydroxyurea, idarubicin hydrochloride, ifosfamide, ilmofosine, improsulfan tosylate, inolimomab, interleukin-2; irinotecan, jm-216, letrozole, lithium gamolenate, lobaplatin, lomustine, lonidamine, mafosfamide, meiphalan, menogaril, mercaptopurine, methotrexate, methotrexate sodium, miboplatin, miltefosine, misonidazole, mitobronitol, mitoguazone dihydrochioride, mitolactol, mitomycin, mitotane, mitozanetrone hydrochloride, mizoribine, mopidamol, muitlaichilpeptide, muromonab-cd3, mustine hydrochloride, mycophenolic acid, mycophenolate mofetil, nedaplatin, nilutamide, nimustine hydrochloride, oxaliplatin, paclitaxel, pcnu, penostatin, peplomycin sulphate, pipobroman, pirarubicin, piritrexim isethionate, piroxantrone hydrochloride, plicamycin, porfimer sodium, prednimustine, procarbazine hydrochloride, raltitrexed, ranimustine, razoxane, rogletimide, roquinimex, sebriplatin, semustine, sirolimus, sizofiran, sobuzoxane, sodium bromebrate, sorafenib, sparfosic acid, sparfosate sodium, sreptozocin, sulofenur, tacrolimus, tamoxifen, tegafur, teloxantrone hydrochloride, temozolomide, teniposide, testolactone, tetrasodium mesotetraphenylporphinesulphonate, thioguanine, thioinosine, thiotepa, topotecan, toremifene, treosulfan, trimetrexate, trofosfamide, tumor necrosis factor, ubenimex, uramustine, vinblastine sulphate, vincristine sulphate, vindesine sulphate, vinorelbine tartrate, vorozole, zinostatin, zolimomab aritox, and zorubicin hydrochloride, and the like, either individually or in any combination, an inhibitor of protein kinase A (PKA), an inhibitor of cAMP signaling, an inhibitor of a PKC (epsilon or alpha or beta) protein kinase, an inhibitor of Bcl-2 (Bcl-2, or MCL-1, or Bcl-xL), a nonsteroidal anti-inflammatory drug, a prostaglandin synthesis inhibitor, a local anesthetic, an anticonvulsant, an antidepressant, an opioid receptor agonist, and a neuroleptic, a benzodiazepine, a barbiturate, a neurosteroid and a inhalation anesthetic, an anesthetic and another pain killer.

The foregoing detailed description has been given for clearness of understanding only and no unnecessary limitations should be understood therefrom as modifications will be obvious to those skilled in the art. It is not an admission that any of the information provided herein is prior art or relevant to the presently claimed disclosures, or that any publication specifically or implicitly referenced is prior art.

Embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed is:

1. A compound having a structural formula (I):

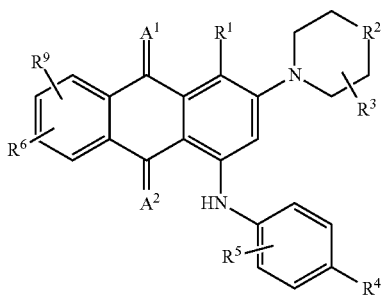

or a salt, or solvate thereof;
wherein:
$A^1$ and $A^2$ are independently oxygen or sulfur;
$R^1$ is selected from the group consisting of hydrogen, —$(CH_2)_n$halogen, —CN, —$CH_3$, $NH_2$, $NHR^a$, $C_{1-6}$ alkyl, $N(CHR)_nC_{3-10}$cycloalkyl, wherein said cycloalkyl can be independently optionally substituted with 1 or 2 groups of $C_{1-6}$ alkyl, halogen, CN, $NO_2$, $NH_2$, $NHR^a$, $SO_2R^{11}$, and $NR^aSO_2R^{11}$;
R is selected from Hydrogen, halogen, CN, $NO_2$, $NH_2$, or $C_{1-6}$ alkyl;
$R^2$ is selected from the group consisting of:

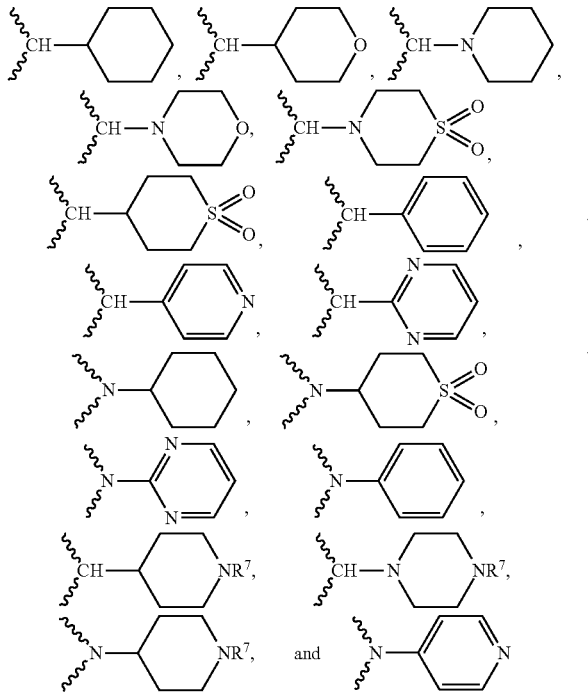

wherein each recited $R^2$ cycloalkyl or heterocycle can be independently optionally substituted with 1 or 2 groups of $C_{1-6}$ alkyl, halogen, CN, $NO_2$, $NH_2$, $NHR^a$, $SO_2R^{11}$, and
$R^3$, $R^5$, $R^6$, and $R^9$ are independently $R^7$;
$R^4$ is selected from the group consisting of: halogen, CN, $NO_2$, $CF_3$, —$(CHR)_nCOOR^{11}$, —$(CHR)_nSO_2R^{11}$, $C_{1-4}$ haloalkyl, —$OC_{1-4}$-haloalkyl, $C_{2-6}$ alkyl, —$(CHR)_nC$(O)$CF_3$, —$(CHR)_nC$(OH)$(CF_3)_2$, —$(CH_2)_n$halogen, —$OR^{10}$, —$NR^{11}R^{12}$, —$NR^aCOR^{11}$, —$NR^aCOOR^{11}$, —$NR^aSO_2R^{11}$, —$NR^aCONR^{11}R^{12}$, —$COR^{11}$, tetrazole, —$(CHR)_n$tetrazole, —S—$C_{1-6}$ alkyl, or —$CONR^{11}R^{12}$, —C(O)$OR^{11}$, —$SO_2NHC$(=O)$CH_3$, —$C(CF_3)(CF_3)OH$, —$SO_2NH_2$, —C(O)$CF_3$, $R^7$ and $R^{10}$ are independently selected from the group consisting of: hydrogen, halogen, CN, $NH_2$, $NO_2$, $C_{1-4}$ haloalkyl, —$OC_{1-4}$ haloalkyl, $C_{1-6}$ alkyl, —C(O)$CF_3$, —$(CH_2)_n$halogen, —$OR^a$, and $NR^aR^a$;
$R^{11}$ and $R^{12}$ are independently selected from the group consisting of: hydrogen, $NR^aC$(=O)R, halogen, CN, $NH_2$, $NHR^a$, $NO_2$, $C_{1-4}$ haloalkyl, —$OC_{1-4}$ haloalkyl, $C_{1-6}$ alkyl, —S—$C_{1-6}$ alkyl, —C(=O)—(O)$_n$—$R^a$, and —$OR^a$, wherein one or more carbon atoms of said alkyl may be replaced with one or more heteroatoms selected from the group consisting of nitrogen, oxygen, and sulfur;
$R^a$ each independently represents hydrogen or $C_{1-6}$ alkyl; and
n represents an integer from 0 to 3.

2. The compound according to claim 1, which is selected from the group consisting of:
4-{[4-amino-3-(4-cyclohexylpiperazin-1-yl)-9,10-dioxo-9,10-dihydroanthracen-1-yl]amino}benzenesulfonamide;
4-{[4-amino-3-(4-cyclohexylpiperazin-1-yl)-9,10-dioxo-9,10-dihydroanthracen-1-yl]amino}benzoic acid;
N-[(4-{[4-amino-3-(4-cyclohexylpiperazin-1-yl)-9,10-dioxo-9,10-dihydroanthracen-1-yl]amino}phenyl)sulfonyl]acetamide;
1-amino-2-(4-cyclohexylpiperazin-1-yl)-4-{[4-(2H-tetrazol-5-yl)phenyl]amino}anthracene-9,10-dione;
1-amino-2-(4-cyclohexylpiperazin-1-yl)-4-{[4-(1H-tetrazol-5-yl)phenyl]amino}anthracene-9,10-dione;
1-amino-2-(4-cyclohexylpiperazin-1-yl)-4-{[4-(1,1,1,3,3,3-hexafluoro-2-hydroxypropan-2-yl)phenyl]amino anthracene-9,10-dione;
methyl 4-[4-amino-3-(4-cyclohexylpiperazin-1-yl)-9,10-dioxo-9,10-dihydroanthracen-1-yl]amino}benzoate;
2-(dimethylamino)ethyl 4-{[4-amino-3-(4-cyclohexylpiperazin-1-yl)-9,10-dioxo-9,10-dihydroanthracen-1-yl]amino}benzoate;
ethyl 4-{[4-amino-3-(4-cyclohexylpiperazin-1-yl)-9,10-dioxo-9,10-dihydroanthracen-1-yl]amino}benzoate;
4-{[4-amino-3-(1,4'-bipiperidin-1'-yl)-9,10-dioxo-9,10-dihydroanthracen-1-yl]amino}benzenesulfonamide;
4-{[4-amino-3-(1,4'-bipiperidin-1'-yl)-9,10-dioxo-9,10-dihydroanthracen-1-yl]amino}benzoic acid;
N-[(4-{[4-amino-3-(1,4'-bipiperidin-1'-yl)-9,10-dioxo-9,10-dihydroanthracen-1-yl]amino}phenyl)sulfonyl]acetamide;

1-amino-2-(1,4'-bipiperidin-1'-yl)-4-{[4-(2H-tetrazol-5-yl)phenyl]amino}anthracene-9,10-dione;

2-(dimethylamino)ethyl 4-{[4-amino-3-(1,4'-bipiperidin-1'-yl)-9,10-dioxo-9,10-dihydroanthracen-1-yl]amino}benzoate; and 1-amino-2-(1,4'-bipiperidin-1'-yl)-4-{[4-(1,1,1,3,3,3-hexafluoro-2-hydroxypropan-2-yl)phenyl]amino}anthracene-9,10-dione, or a salt, or solvate thereof.

3. The compound according to claim 1, which is:

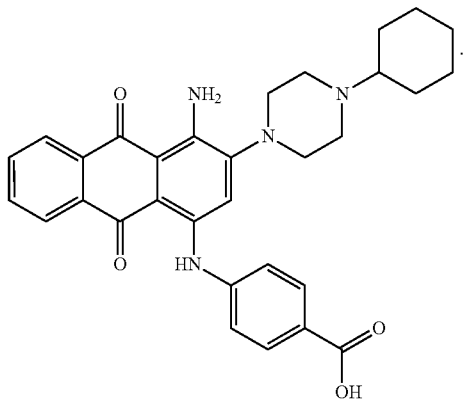

4. A compound having a structural formula (II):

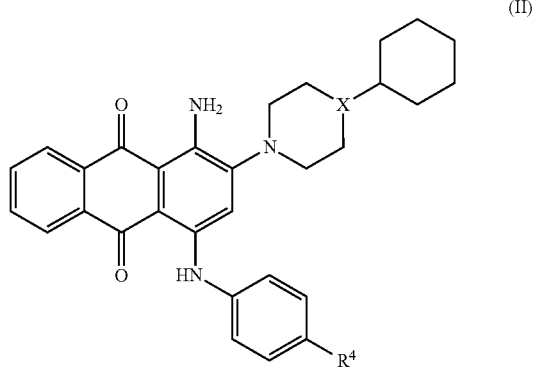

(II)

or a salt, or solvate thereof;
wherein:
X represents N or CH;
R⁴ is selected from the group consisting of: —C(O)OR¹¹, —C(CF₃)(CF₃)OH, —CF₃, —(CHR)$_n$COOR¹¹, —(CHR)$_n$SO₂R¹¹, —(CHR)$_n$C(OH)(CF₃)₂,

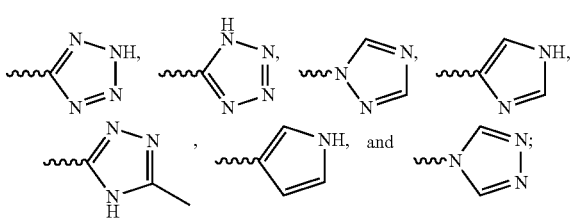

R¹¹ is selected from the group consisting of: hydrogen, NR$^a$C(=O)R, halogen, CN, NH₂, NHR$^a$, NO₂, C$_{1-4}$ haloalkyl, —OC$_{1-4}$ haloalkyl, —S—C$_{1-6}$ alkyl, —C(=O)—(O)$_n$—R$^a$, —OR$^a$, or C$_{1-6}$ alkyl, wherein one or more carbon atoms of said alkyl may be replaced with one or more heteroatoms selected from the group consisting of nitrogen, oxygen, and sulfur;

R represents hydrogen, halogen, CN, NO₂, or C$_{1-6}$ alkyl;

R$^a$ each independently represents hydrogen or C$_{1-6}$ alkyl; and n represents 0.

5. The compound according to claim 4, which is selected from the group consisting of:
4-{[4-amino-3-(4-cyclohexylpiperazin-1-yl)-9,10-dioxo-9,10-dihydroanthracen-1-yl]amino}benzenesulfonamide;
4-{[4-amino-3-(4-cyclohexylpiperazin-1-yl)-9,10-dioxo-9,10-dihydroanthracen-1-yl]amino}benzoic acid;
N-[(4-{[4-amino-3-(4-cyclohexylpiperazin-1-yl)-9,10-dioxo-9,10-dihydroanthracen-1-yl]amino}phenyl)sulfonyl]acetamide;
1-amino-2-(4-cyclohexylpiperazin-1-yl)-4-{[4-(2H-tetrazol-5-yl)phenyl]amino}anthracene-9,10-dione;
1-amino-2-(4-cyclohexylpiperazin-1-yl)-4-{[4-(1H-tetrazol-5-yl)phenyl]amino}anthracene-9,10-dione;
1-amino-2-(4-cyclohexylpiperazin-1-yl)-4-{[4-(1,1,1,3,3,3-hexafluoro-2-hydroxypropan-2-yl)phenyl]amino}anthracene-9,10-dione;
methyl 4-{[4-amino-3-(4-cyclohexylpiperazin-1-yl)-9,10-dioxo-9,10-dihydroanthracen-1-yl]amino}benzoate;
2-(dimethylamino)ethyl 4-{[4-amino-3-(4-cyclohexylpiperazin-1-yl)-9,10-dioxo-9,10-dihydroanthracen-1-yl]amino}benzoate; and
ethyl 4-{[4-amino-3-(4-cyclohexylpiperazin-1-yl)-9,10-dioxo-9,10-dihydroanthracen-1-yl]amino}benzoate;
or a salt, or solvate thereof.

6. A pharmaceutical composition, comprising:
a) a therapeutically effective amount of a compound according to claim 1, or a salt, or solvate thereof; and
b) a pharmaceutically acceptable vehicle or carrier.

7. The pharmaceutical composition according to claim 6, wherein the compound is selected from the group consisting of:
4-{[4-amino-3-(4-cyclohexylpiperazin-1-yl)-9,10-dioxo-9,10-dihydroanthracen-1-yl]amino}benzenesulfonamide;
4-{[4-amino-3-(4-cyclohexylpiperazin-1-yl)-9,10-dioxo-9,10-dihydroanthracen-1-yl]amino}benzoic acid;
N-[(4-{[4-amino-3-(4-cyclohexylpiperazin-1-yl)-9,10-dioxo-9,10-dihydroanthracen-1-yl]amino}phenyl)sulfonyl]acetamide;
1-amino-2-(4-cyclohexylpiperazin-1-yl)-4-{[4-(2H-tetrazol-5-yl)phenyl]amino}anthracene-9,10-dione;
1-amino-2-(4-cyclohexylpiperazin-1-yl)-4-{[4-(1H-tetrazol-5-yl)phenyl]amino}anthracene-9,10-dione;
1-amino-2-(4-cyclohexylpiperazin-1-yl)-4-{[4-(1,1,1,3,3,3-hexafluoro-2-hydroxypropan-2-yl)phenyl]amino}anthracene-9,10-dione;
methyl 4-{[4-amino-3-(4-cyclohexylpiperazin-1-yl)-9,10-dioxo-9,10-dihydroanthracen-1-yl]amino}benzoate;
2-(dimethylamino)ethyl 4-{[4-amino-3-(4-cyclohexylpiperazin-1-yl)-9,10-dioxo-9,10-dihydroanthracen-1-yl]amino}benzoate;
ethyl 4-{[4-amino-3-(4-cyclohexylpiperazin-1-yl)-9,10-dioxo-9,10-dihydroanthracen-1-yl]amino}benzoate;
4-{[4-amino-3-(1,4'-bipiperidin-1'-yl)-9,10-dioxo-9,10-dihydroanthracen-1-yl]amino}benzenesulfonamide;
4-{[4-amino-3-(1,4'-bipiperidin-1'-yl)-9,10-dioxo-9,10-dihydroanthracen-1-yl]amino}benzoic acid;

N-[(4-{[4-amino-3-(1,4'-bipiperidin-1'-yl)-9,10-dioxo-9,10-dihydroanthracen-1-yl]amino}phenyl)sulfonyl]acetamide;

1-amino-2-(1,4'-bipiperidin-1'-yl)-4-{[4-(2H-tetrazol-5-yl)phenyl]amino}anthracene-9,10-dione;

2-(dimethylamino)ethyl 4-{[4-amino-3-(1,4'-bipiperidin-1'-yl)-9,10-dioxo-9,10-dihydroanthracen-1-yl]amino}benzoate; and 1-amino-2-(1,4'-bipiperidin-1'-yl)-4-{[4-(1,1,1,3,3,3-hexafluoro-2-hydroxypropan-2-yl)phenyl]amino}anthracene-9,10-dione, or a salt, or solvate thereof.

8. The pharmaceutical composition according to claim 6, wherein the compound is:

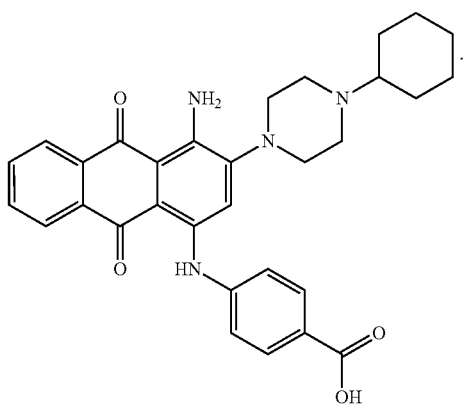 [SMILES: Nc1c(N2CCN(C3CCCCC3)CC2)cc(Nc2ccc(C(=O)O)cc2)c2c1C(=O)c1ccccc1C2=O]

9. The pharmaceutical composition according to claim 6, wherein said pharmaceutical composition is formulated in a unit dosage form selected from the group consisting of:
an oral unit dosage form, an injection unit dosage form, a transdermal patch unit dosage form, or an implantation of a depot formulation unit dosage form.

10. A pharmaceutical composition, comprising:
a) a therapeutically effective amount of a compound according to claim 4, or a salt, or solvate thereof; and
b) a pharmaceutically acceptable vehicle or carrier.

11. The pharmaceutical composition according to claim 10, wherein the compound is selected from the group consisting of:
4-{[4-amino-3-(4-cyclohexylpiperazin-1-yl)-9,10-dioxo-9,10-dihydroanthracen-1-yl]amino}benzenesulfonamide;
4-{[4-amino-3-(4-cyclohexylpiperazin-1-yl)-9,10-dioxo-9,10-dihydroanthracen-1-yl]amino}benzoic acid;
N-[(4-{[4-amino-3-(4-cyclohexylpiperazin-1-yl)-9,10-dioxo-9,10-dihydroanthracen-1-yl]amino}phenyl)sulfonyl]acetamide;
1-amino-2-(4-cyclohexylpiperazin-1-yl)-4-{[4-(2H-tetrazol-5-yl)phenyl]amino}anthracene-9,10-dione;
1-amino-2-(4-cyclohexylpiperazin-1-yl)-4-{[4-(1H-tetrazol-5-yl)phenyl]amino}anthracene-9,10-dione;
1-amino-2-(4-cyclohexylpiperazin-1-yl)-4-{[4-(1,1,1,3,3,3-hexafluoro-2-hydroxypropan-2-yl)phenyl]amino}anthracene-9,10-dione;
methyl 4-{[4-amino-3-(4-cyclohexylpiperazin-1-yl)-9,10-dioxo-9,10-dihydroanthracen-1-yl]amino}benzoate;
2-(dimethylamino)ethyl 4-{[4-amino-3-(4-cyclohexylpiperazin-1-yl)-9,10-dioxo-9,10-dihydroanthracen-1-yl]amino}benzoate; and
ethyl 4-{[4-amino-3-(4-cyclohexylpiperazin-1-yl)-9,10-dioxo-9,10-dihydroanthracen-1-yl]amino}benzoate;
or a salt, or solvate thereof.

12. The pharmaceutical composition according to claim 10, wherein said pharmaceutical composition is formulated in a unit dosage form selected from the group consisting of:
an oral unit dosage form, an injection unit dosage form, a transdermal patch unit dosage form, or an implantation of a depot formulation unit dosage form.

13. The pharmaceutical composition according to claim 12, wherein the compound is:

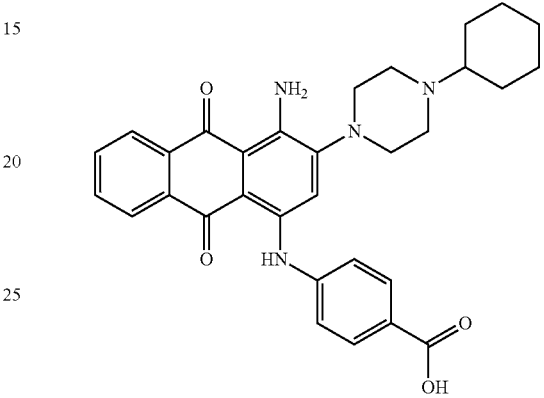

14. A method for ameliorating pain in a patient suffering therefrom, comprising:
a) administering to the patient a therapeutically effective amount of a compound according to claim 1, or a pharmaceutically acceptable salt, or solvate thereof, and
wherein the pain is selected from the group consisting of: acute pain, chronic pain, inflammatory pain, neuropathic pain, tonic pain, persistent pain, postoperative pain, osteoarthritis pain, diabetic neuropathic pain, chemical-induced pain, chemotherapy-induced pain, cancer-pain, drug-induced pain, bone pain, pain associated with alcohol-induced hyperalgesia, a generalized pain disorder, and combinations thereof.

15. A method for ameliorating acute or chronic pain in a patient suffering therefrom, comprising:
a) administering to the patient a therapeutically effective amount of a compound according to claim 4, or a pharmaceutically acceptable salt, or solvate thereof.

16. The method according to claim 14, wherein the compound administered is selected from the group consisting of:
4-{[4-amino-3-(4-cyclohexylpiperazin-1-yl)-9,10-dioxo-9,10-dihydroanthracen-1-yl]amino}benzenesulfonamide;
4-{[4-amino-3-(4-cyclohexylpiperazin-1-yl)-9,10-dioxo-9,10-dihydroanthracen-1-yl]amino}benzoic acid;
N-[(4-{[4-amino-3-(4-cyclohexylpiperazin-1-yl)-9,10-dioxo-9,10-dihydroanthracen-1-yl]amino}phenyl)sulfonyl]acetamide;
1-amino-2-(4-cyclohexylpiperazin-1-yl)-4-{[4-(2H-tetrazol-5-yl)phenyl]amino}anthracene-9,10-dione;
1-amino-2-(4-cyclohexylpiperazin-1-yl)-4-{[4-(1H-tetrazol-5-yl)phenyl]amino}anthracene-9,10-dione;
1-amino-2-(4-cyclohexylpiperazin-1-yl)-4-{[4-(1,1,1,3,3,3-hexafluoro-2-hydroxypropan-2-yl)phenyl]amino}anthracene-9,10-dione;
methyl 4-{[4-amino-3-(4-cyclohexylpiperazin-1-yl)-9,10-dioxo-9,10-dihydroanthracen-1-yl]amino}benzoate;

2-(dimethylamino)ethyl 4-{[4-amino-3-(4-cyclohexylpiperazin-1-yl)-9,10-dioxo-9,10-dihydroanthracen-1-yl]amino}benzoate;
ethyl 4-{[4-amino-3-(4-cyclohexylpiperazin-1-yl)-9,10-dioxo-9,10-dihydroanthracen-1-yl]amino}benzoate;
4-{[4-amino-3-(1,4'-bipiperidin-1'-yl)-9,10-dioxo-9,10-dihydroanthracen-1-yl]amino}benzenesulfonamide;
4-{[4-amino-3-(1,4'-bipiperidin-1'-yl)-9,10-dioxo-9,10-dihydroanthracen-1-yl]amino}benzoic acid;
N-[(4-{[4-amino-3-(1,4'-bipiperidin-1'-yl)-9,10-dioxo-9,10-dihydroanthracen-1-yl]amino}phenyl)sulfonyl]acetamide;
1-amino-2-(1,4'-bipiperidin-1'-yl)-4-{[4-(2H-tetrazol-5-yl)phenyl]amino}anthracene-9,10-dione;
2-(dimethylamino)ethyl 4-{[4-amino-3-(1,4'-bipiperidin-1'-yl)-9,10-dioxo-9,10-dihydroanthracen-1-yl]amino}benzoate; and
1-amino-2-(1,4'-bipiperidin-1'-yl)-4-{[4-(1,1,1,3,3,3-hexafluoro-2-hydroxypropan-2-yl)phenyl]amino}anthracene-9,10-dione,
or a salt, or solvate thereof.

17. The method according to claim 14, wherein the compound administered is:

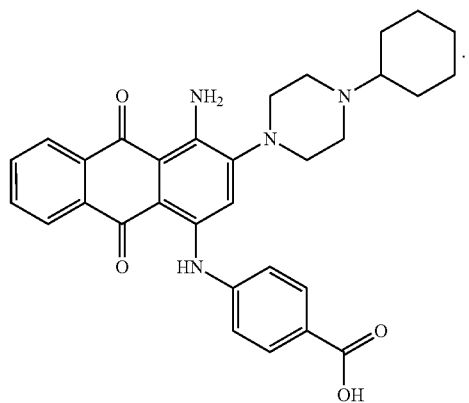 [SMILES: Nc1c(N2CCN(C3CCCCC3)CC2)cc(Nc2ccc(C(=O)O)cc2)c2c1C(=O)c1ccccc1C2=O]

18. The method according to claim 15, wherein the compound administered is selected from the group consisting of:
4-{[4-amino-3-(4-cyclohexylpiperazin-1-yl)-9,10-dioxo-9,10-dihydroanthracen-1-yl]amino}benzenesulfonamide;
4-{[4-amino-3-(4-cyclohexylpiperazin-1-yl)-9,10-dioxo-9,10-dihydroanthracen-1-yl]amino}benzoic acid;
N-[(4-{[4-amino-3-(4-cyclohexylpiperazin-1-yl)-9,10-dioxo-9,10-dihydroanthracen-1-yl]amino}phenyl)sulfonyl]acetamide;
1-amino-2-(4-cyclohexylpiperazin-1-yl)-4-{[4-(2H-tetrazol-5-yl)phenyl]amino}anthracene-9,10-dione;
1-amino-2-(4-cyclohexylpiperazin-1-yl)-4-{[4-(1H-tetrazol-5-yl)phenyl]amino}anthracene-9,10-dione;
1-amino-2-(4-cyclohexylpiperazin-1-yl)-4-{[4-(1,1,1,3,3,3-hexafluoro-2-hydroxypropan-2-yl)phenyl]amino}anthracene-9,10-dione;
methyl 4-{[4-amino-3-(4-cyclohexylpiperazin-1-yl)-9,10-dioxo-9,10-dihydroanthracen-1-yl]amino}benzoate;
2-(dimethylamino)ethyl 4-{[4-amino-3-(4-cyclohexylpiperazin-1-yl)-9,10-dioxo-9,10-dihydroanthracen-1-yl]amino}benzoate; and
ethyl 4-{[4-amino-3-(4-cyclohexylpiperazin-1-yl)-9,10-dioxo-9,10-dihydroanthracen-1-yl]amino}benzoate;
or a salt, or solvate thereof.

19. The method according to claim 15, wherein the compound administered is:

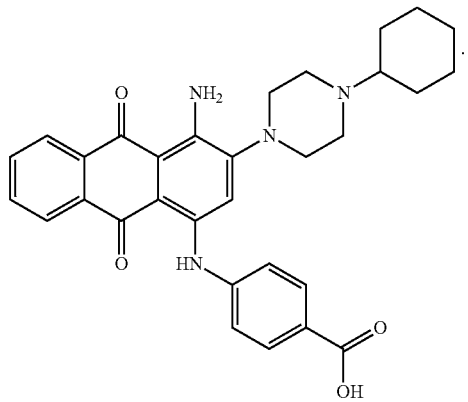 [SMILES: Nc1c(N2CCN(C3CCCCC3)CC2)cc(Nc2ccc(C(=O)O)cc2)c2c1C(=O)c1ccccc1C2=O]

20. A synergistic method for reducing tumor growth of a pancreatic cancer in a patient suffering therefrom, comprising:
a) administering to the patient a therapeutically effective amount of gemcitabine; and
b) administering to the patient a therapeutically effective amount a compound having the following structure:

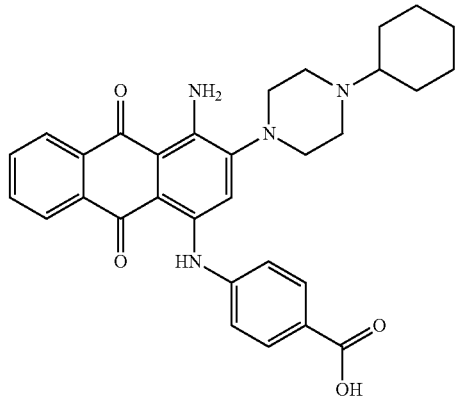

or a pharmaceutically acceptable salt, or solvate thereof, wherein the combination of gemcitabine and the aforementioned compound exhibit a synergistic effect on tumor reduction.

* * * * *

UNITED STATES PATENT AND TRADEMARK OFFICE
CERTIFICATE OF CORRECTION

Page 1 of 1

PATENT NO. : 9,346,788 B2
APPLICATION NO. : 14/614917
DATED : May 24, 2016
INVENTOR(S) : Jay Jie-Qiang Wu It is certified that error appears in the above-identified patent and that said Letters Patent is hereby corrected as shown below:

IN THE CLAIMS:

In column 53, line 63, of Claim 1, after "$SO_2R^{11}$, and" please add the following text:
--$NR^aSO_2R^{11}$,--

In column 56, line 6, of Claim 4, after "$NO_2$," and before "or $C_{1-6}$ alkyl;" please add the following text:
--$NH_2$,--

Signed and Sealed this
Sixteenth Day of August, 2016

Michelle K. Lee
*Director of the United States Patent and Trademark Office*